US012186494B2

(12) United States Patent
Howell et al.

(10) Patent No.: US 12,186,494 B2
(45) Date of Patent: Jan. 7, 2025

(54) GUIDEWIRE-MANAGEMENT DEVICES AND METHODS THEREOF

(71) Applicant: Bard Access Systems, Inc., Salt Lake City, UT (US)

(72) Inventors: Glade H. Howell, Draper, UT (US); Kyle G. Thornley, Farmington, UT (US); Juan Sepulveda, Centerville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 522 days.

(21) Appl. No.: 17/200,630

(22) Filed: Mar. 12, 2021

(65) Prior Publication Data

US 2021/0283368 A1 Sep. 16, 2021

Related U.S. Application Data

(60) Provisional application No. 62/989,397, filed on Mar. 13, 2020.

(51) Int. Cl.
*A61M 25/09* (2006.01)
*A61M 25/00* (2006.01)

(52) U.S. Cl.
CPC .... *A61M 25/002* (2013.01); *A61M 25/09041* (2013.01)

(58) Field of Classification Search
CPC ............ A61M 25/09; A61M 25/09041; A61M 25/0111; A61M 25/002; A61M 25/0113;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

CN 202526749 U 11/2012
EP 0641571 A1 3/1995
(Continued)

OTHER PUBLICATIONS

PCT/US2020/057202 filed Oct. 23, 2020 International Preliminary Report on Patentability dated Apr. 26, 2022.
(Continued)

*Primary Examiner* — Laura A Bouchelle
*Assistant Examiner* — Sarah Dympna Grasmeder
(74) *Attorney, Agent, or Firm* — Rutan & Tucker LLP

(57) ABSTRACT

Guidewire-management devices and systems thereof are disclosed herein. A guidewire-management device can include a guidewire, a first sleeve, and a second sleeve. The first sleeve can be configured for distally feeding the guidewire out of the guidewire-management device. The first sleeve can also be configured for proximally feeding the guidewire into the guidewire-management device. The second sleeve can be proximal of the first sleeve in the guidewire-management device. The second sleeve can be configured for feeding the guidewire in concert with the first sleeve. At least a length of the guidewire extending between the first sleeve and the second sleeve can be disposed within a sterile barrier configured to maintain sterility of the guidewire.

10 Claims, 24 Drawing Sheets

Figure 1:
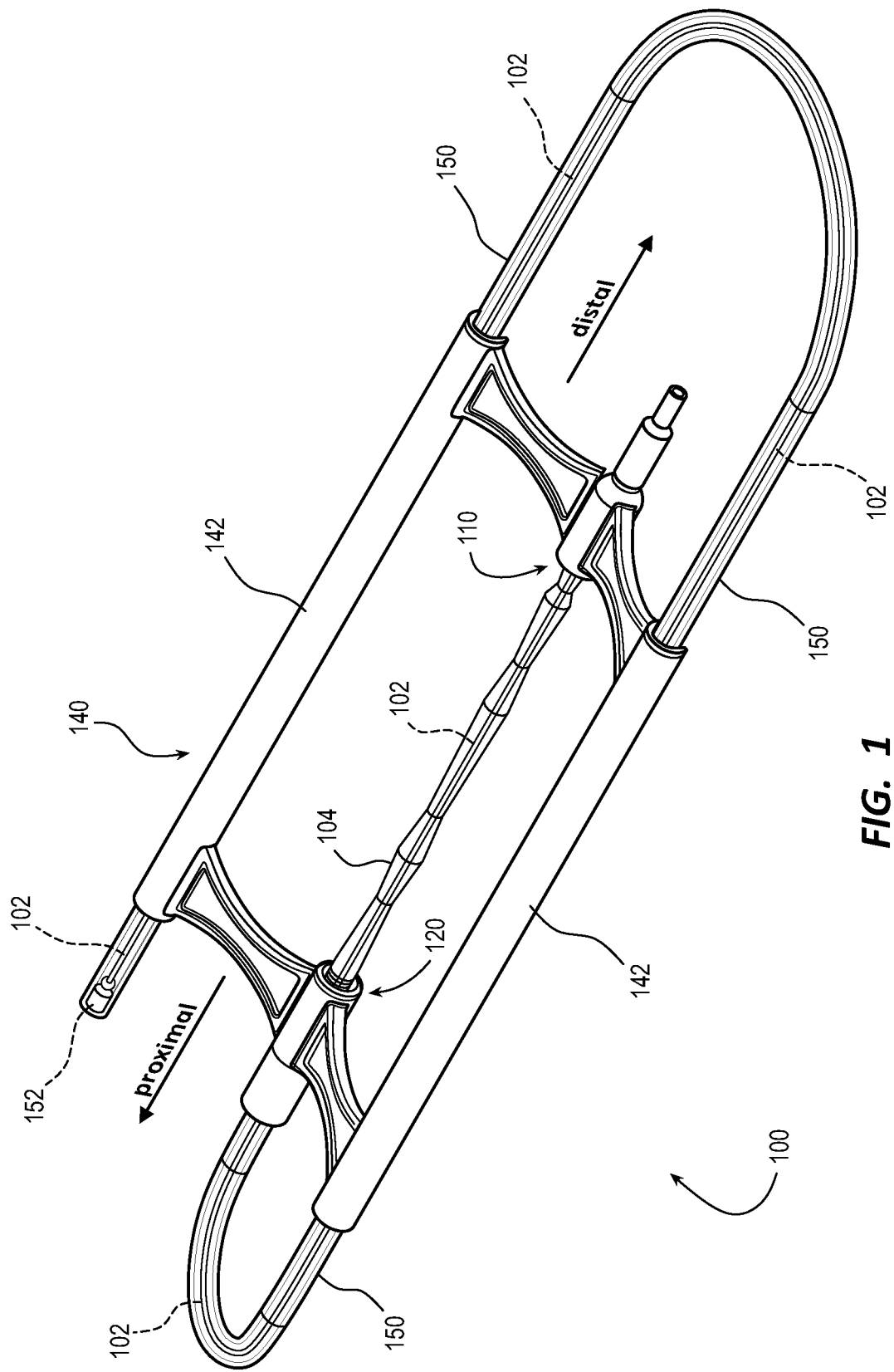

(58) Field of Classification Search
CPC .... A61M 25/0668; A61M 2025/09175; A61M 2025/09116; A61M 2025/0034; A61B 50/30; A61B 50/00; A61B 2050/0065
See application file for complete search history.

(56) References Cited

U.S. PATENT DOCUMENTS

| | | | |
|---|---|---|---|
| 3,890,976 A | 6/1975 | Bazell et al. | |
| 4,051,849 A * | 10/1977 | Poncy | A61M 25/0111 604/528 |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 4,637,404 A | 1/1987 | Gessman | |
| 4,840,613 A | 6/1989 | Balbierz | |
| 4,935,008 A | 6/1990 | Lewis, Jr. | |
| 4,995,872 A | 2/1991 | Ferrara | |
| 5,017,259 A | 5/1991 | Kohsai | |
| 5,040,548 A | 8/1991 | Yock | |
| 5,057,073 A | 10/1991 | Martin | |
| 5,112,312 A | 5/1992 | Luther | |
| 5,120,317 A | 6/1992 | Luther | |
| 5,188,593 A | 2/1993 | Martin | |
| 5,195,962 A | 3/1993 | Martin et al. | |
| 5,207,650 A | 5/1993 | Martin | |
| 5,263,938 A | 11/1993 | Orr et al. | |
| 5,267,958 A | 12/1993 | Buchbinder et al. | |
| 5,273,042 A * | 12/1993 | Lynch | A61M 25/09041 604/164.08 |
| 5,282,479 A | 2/1994 | Havran | |
| 5,295,970 A | 3/1994 | Clinton et al. | |
| 5,306,247 A | 4/1994 | Pfenninger | |
| 5,328,472 A | 7/1994 | Steinke et al. | |
| 5,350,358 A | 9/1994 | Martin | |
| 5,363,847 A | 11/1994 | Viera | |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,420,882 A | 5/1995 | Black | |
| 5,439,449 A | 8/1995 | Mapes et al. | |
| 5,443,457 A | 8/1995 | Ginn et al. | |
| 5,489,271 A | 2/1996 | Andersen | |
| 5,573,520 A | 11/1996 | Schwartz et al. | |
| 5,683,370 A | 11/1997 | Luther et al. | |
| 5,718,678 A | 2/1998 | Fleming, III | |
| 5,772,636 A | 6/1998 | Brimhall et al. | |
| 5,827,202 A | 10/1998 | Miraki et al. | |
| 5,885,251 A | 3/1999 | Luther | |
| 5,919,164 A | 7/1999 | Andersen | |
| 5,947,940 A | 9/1999 | Beisel | |
| 5,957,893 A | 9/1999 | Luther et al. | |
| 6,123,084 A | 9/2000 | Jandak et al. | |
| 6,206,849 B1 | 3/2001 | Martin et al. | |
| 6,228,062 B1 * | 5/2001 | Howell | A61M 25/0668 604/165.01 |
| 6,475,187 B1 | 11/2002 | Gerberding | |
| 6,606,515 B1 | 8/2003 | Windheuser et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,770 B2 | 12/2010 | Raulerson et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 | 11/2013 | Kronfeld et al. | |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,522,254 B2 | 12/2016 | Belson | |
| 9,554,785 B2 | 1/2017 | Walters et al. | |
| 9,566,087 B2 | 2/2017 | Bierman et al. | |
| 9,579,484 B2 | 2/2017 | Barnell | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutilette et al. | |
| 9,820,845 B2 | 11/2017 | von Lehe et al. | |
| 9,861,383 B2 | 1/2018 | Clark | |
| 9,884,169 B2 | 2/2018 | Bierman et al. | |
| 9,889,275 B2 | 2/2018 | Voss et al. | |
| 9,913,585 B2 | 3/2018 | McCaffrey et al. | |
| 9,913,962 B2 | 3/2018 | Tal et al. | |
| 9,981,113 B2 | 5/2018 | Bierman | |
| 10,010,312 B2 | 7/2018 | Tegels | |
| 10,065,020 B2 | 9/2018 | Gaur | |
| 10,098,724 B2 | 10/2018 | Adams et al. | |
| 10,111,683 B2 | 10/2018 | Tsamir et al. | |
| 10,118,020 B2 | 11/2018 | Avneri et al. | |
| 10,130,269 B2 | 11/2018 | McCaffrey et al. | |
| 10,220,184 B2 | 3/2019 | Clark | |
| 10,220,191 B2 | 3/2019 | Belson et al. | |
| 10,265,508 B2 | 4/2019 | Baid | |
| 10,271,873 B2 | 4/2019 | Steingisser et al. | |
| 10,376,675 B2 | 8/2019 | Mitchell et al. | |
| 10,675,440 B2 | 6/2020 | Abitabilo et al. | |
| 10,806,901 B2 | 10/2020 | Burkholz et al. | |
| 11,285,301 B2 | 3/2022 | Ornelas Vargas et al. | |
| 2002/0040231 A1 | 4/2002 | Wysoki | |
| 2002/0198492 A1 | 12/2002 | Miller et al. | |

(56) References Cited

U.S. PATENT DOCUMENTS

| | | | |
|---|---|---|---|
| 2003/0036712 A1* | 2/2003 | Heh | A61M 25/09041 604/95.04 |
| 2003/0060863 A1 | 3/2003 | Dobak | |
| 2003/0088212 A1 | 5/2003 | Tal | |
| 2003/0100849 A1 | 5/2003 | Jang | |
| 2003/0153874 A1 | 8/2003 | Tal | |
| 2003/0158514 A1 | 8/2003 | Tal | |
| 2004/0116901 A1 | 6/2004 | Appling | |
| 2004/0193093 A1 | 9/2004 | Desmond | |
| 2004/0230178 A1 | 11/2004 | Wu | |
| 2005/0004554 A1 | 1/2005 | Osborne | |
| 2005/0245847 A1 | 11/2005 | Schaeffer | |
| 2005/0245882 A1 | 11/2005 | Elkins et al. | |
| 2005/0283221 A1 | 12/2005 | Mann et al. | |
| 2006/0009740 A1 | 1/2006 | Higgins et al. | |
| 2006/0064036 A1 | 3/2006 | Osborne et al. | |
| 2006/0116629 A1 | 6/2006 | Tal et al. | |
| 2006/0129100 A1 | 6/2006 | Tal | |
| 2006/0129130 A1 | 6/2006 | Tal et al. | |
| 2007/0276288 A1 | 11/2007 | Khaw | |
| 2008/0045894 A1 | 2/2008 | Perchik et al. | |
| 2008/0058839 A1 | 3/2008 | Nobles et al. | |
| 2008/0091137 A1 | 4/2008 | Reavill | |
| 2008/0125744 A1 | 5/2008 | Treacy | |
| 2008/0125748 A1 | 5/2008 | Patel | |
| 2008/0262430 A1 | 10/2008 | Anderson et al. | |
| 2008/0262431 A1 | 10/2008 | Anderson et al. | |
| 2008/0294111 A1 | 11/2008 | Tal et al. | |
| 2008/0312578 A1 | 12/2008 | DeFonzo et al. | |
| 2009/0105653 A1 | 4/2009 | Spenser et al. | |
| 2009/0221961 A1 | 9/2009 | Tal et al. | |
| 2009/0227900 A1 | 9/2009 | Kim et al. | |
| 2009/0270889 A1 | 10/2009 | Tal et al. | |
| 2010/0256487 A1 | 10/2010 | Hawkins et al. | |
| 2010/0305474 A1 | 12/2010 | DeMars et al. | |
| 2011/0004162 A1 | 1/2011 | Tal | |
| 2011/0009827 A1 | 1/2011 | Bierman et al. | |
| 2011/0021994 A1 | 1/2011 | Anderson et al. | |
| 2011/0066142 A1 | 3/2011 | Tal et al. | |
| 2011/0106057 A1 | 5/2011 | Hamboly | |
| 2011/0144620 A1 | 6/2011 | Tal | |
| 2011/0152836 A1 | 6/2011 | Riopelle et al. | |
| 2011/0202006 A1 | 8/2011 | Bierman et al. | |
| 2011/0251559 A1 | 10/2011 | Tal et al. | |
| 2011/0270192 A1 | 11/2011 | Anderson et al. | |
| 2012/0004665 A1 | 1/2012 | Defossez et al. | |
| 2012/0041371 A1 | 2/2012 | Tal et al. | |
| 2012/0065590 A1 | 3/2012 | Bierman et al. | |
| 2012/0071857 A1 | 3/2012 | Goldfarb et al. | |
| 2012/0078231 A1 | 3/2012 | Hoshinouchi | |
| 2012/0130411 A1 | 5/2012 | Tal et al. | |
| 2012/0130415 A1 | 5/2012 | Tal et al. | |
| 2012/0157854 A1 | 6/2012 | Kurrus et al. | |
| 2012/0220942 A1 | 8/2012 | Hall et al. | |
| 2012/0283640 A1* | 11/2012 | Anderson | A61M 25/09 604/164.1 |
| 2012/0316500 A1 | 12/2012 | Bierman et al. | |
| 2013/0053826 A1 | 2/2013 | Shevgoor | |
| 2013/0123704 A1 | 5/2013 | Bierman et al. | |
| 2013/0158338 A1 | 6/2013 | Kelly et al. | |
| 2013/0188291 A1 | 7/2013 | Vardiman | |
| 2013/0237931 A1 | 9/2013 | Tal et al. | |
| 2013/0306079 A1 | 11/2013 | Tracy | |
| 2014/0025036 A1 | 1/2014 | Bierman et al. | |
| 2014/0081210 A1 | 3/2014 | Bierman et al. | |
| 2014/0100552 A1 | 4/2014 | Gallacher et al. | |
| 2014/0207052 A1 | 7/2014 | Tal et al. | |
| 2014/0207069 A1 | 7/2014 | Bierman et al. | |
| 2014/0214005 A1 | 7/2014 | Belson | |
| 2014/0257111 A1 | 9/2014 | Yamashita et al. | |
| 2014/0276432 A1 | 9/2014 | Bierman et al. | |
| 2014/0276599 A1 | 9/2014 | Cully et al. | |
| 2015/0045695 A1 | 2/2015 | Simpson et al. | |
| 2015/0080939 A1 | 3/2015 | Adams et al. | |
| 2015/0112310 A1 | 4/2015 | Call et al. | |
| 2015/0126930 A1 | 5/2015 | Bierman et al. | |
| 2015/0148595 A1 | 5/2015 | Bagwell et al. | |
| 2015/0190168 A1 | 7/2015 | Bierman et al. | |
| 2015/0196210 A1 | 7/2015 | McCaffrey et al. | |
| 2015/0224287 A1 | 8/2015 | Bian et al. | |
| 2015/0231364 A1 | 8/2015 | Blanchard et al. | |
| 2015/0283357 A1 | 10/2015 | Lampropoulos et al. | |
| 2015/0297867 A1 | 10/2015 | Howell et al. | |
| 2015/0297868 A1 | 10/2015 | Tal et al. | |
| 2015/0320969 A1 | 11/2015 | Haslinger et al. | |
| 2015/0351793 A1 | 12/2015 | Bierman et al. | |
| 2015/0359549 A1 | 12/2015 | Lenker et al. | |
| 2015/0359998 A1 | 12/2015 | Carmel et al. | |
| 2016/0074628 A1* | 3/2016 | Smith | A61B 1/0014 604/174 |
| 2016/0082223 A1 | 3/2016 | Barnell | |
| 2016/0114124 A1 | 4/2016 | Tal | |
| 2016/0220786 A1 | 8/2016 | Mitchell et al. | |
| 2016/0325073 A1 | 11/2016 | Davies et al. | |
| 2016/0338728 A1 | 11/2016 | Tal | |
| 2016/0346503 A1 | 12/2016 | Jackson et al. | |
| 2017/0014599 A1* | 1/2017 | Crisman | A61M 25/0113 |
| 2017/0035990 A1 | 2/2017 | Swift | |
| 2017/0072165 A1 | 3/2017 | Lim et al. | |
| 2017/0080189 A1 | 3/2017 | Tao et al. | |
| 2017/0128700 A1 | 5/2017 | Roche Rebollo | |
| 2017/0172653 A1 | 6/2017 | Urbanski et al. | |
| 2017/0239443 A1 | 8/2017 | Abitabilo et al. | |
| 2017/0273713 A1 | 9/2017 | Shah et al. | |
| 2017/0296792 A1 | 10/2017 | Ornelas Vargas et al. | |
| 2017/0326339 A1 | 11/2017 | Bailey et al. | |
| 2017/0361070 A1 | 12/2017 | Hivert | |
| 2018/0021545 A1 | 1/2018 | Mitchell et al. | |
| 2018/0116690 A1 | 5/2018 | Sarabia et al. | |
| 2018/0117284 A1 | 5/2018 | Appling et al. | |
| 2018/0133438 A1 | 5/2018 | Hulvershorn et al. | |
| 2018/0154062 A1 | 6/2018 | DeFonzo et al. | |
| 2018/0154112 A1 | 6/2018 | Chan et al. | |
| 2018/0296799 A1 | 10/2018 | Horst et al. | |
| 2018/0296804 A1 | 10/2018 | Bierman | |
| 2019/0015646 A1 | 1/2019 | Matlock et al. | |
| 2019/0046770 A1 | 2/2019 | Shields | |
| 2019/0060616 A1 | 2/2019 | Solomon | |
| 2019/0076167 A1 | 3/2019 | Fantuzzi et al. | |
| 2019/0134349 A1 | 5/2019 | Cohn et al. | |
| 2019/0255294 A1 | 8/2019 | Mitchell et al. | |
| 2019/0276268 A1 | 9/2019 | Akingba | |
| 2019/0321590 A1 | 10/2019 | Burkholz et al. | |
| 2020/0016374 A1 | 1/2020 | Burkholz et al. | |
| 2021/0069471 A1 | 3/2021 | Howell | |
| 2021/0085927 A1 | 3/2021 | Howell | |
| 2021/0121661 A1 | 4/2021 | Howell | |
| 2021/0121667 A1 | 4/2021 | Howell | |
| 2021/0228843 A1 | 7/2021 | Howell et al. | |
| 2021/0307854 A1 | 10/2021 | Bernhard et al. | |
| 2021/0322729 A1 | 10/2021 | Howell | |
| 2021/0330941 A1 | 10/2021 | Howell et al. | |
| 2021/0330942 A1 | 10/2021 | Howell | |
| 2021/0361915 A1 | 11/2021 | Howell et al. | |
| 2021/0402149 A1 | 12/2021 | Howell | |
| 2021/0402153 A1 | 12/2021 | Howell et al. | |
| 2022/0001138 A1 | 1/2022 | Howell | |
| 2022/0032013 A1 | 2/2022 | Howell et al. | |
| 2022/0176082 A1 | 6/2022 | Mckinnon et al. | |
| 2022/0193379 A1 | 6/2022 | Howell | |
| 2022/0409275 A1 | 12/2022 | Hoang et al. | |
| 2023/0128853 A1 | 4/2023 | Lindekugel et al. | |
| 2023/0129318 A1 | 4/2023 | Lindekugel et al. | |
| 2023/0277812 A1 | 9/2023 | Howell et al. | |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2433670 A1 | 3/2012 |

(56) References Cited

FOREIGN PATENT DOCUMENTS

| | | | |
|---|---|---|---|
| EP | 2486880 | A2 | 8/2012 |
| EP | 2486881 | A2 | 8/2012 |
| EP | 2486951 | A2 | 8/2012 |
| EP | 2512576 | A2 | 10/2012 |
| EP | 2152348 | B1 | 2/2015 |
| EP | 3205368 | A1 | 8/2017 |
| EP | 3093038 | B1 | 5/2019 |
| EP | 2260897 | B1 | 9/2019 |
| GB | 1273547 | A | 5/1972 |
| WO | 9306878 | A1 | 4/1993 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 02/05886 | A1 | 1/2002 |
| WO | 2003008020 | A1 | 1/2003 |
| WO | 2003057272 | A2 | 7/2003 |
| WO | 2003066125 | A2 | 8/2003 |
| WO | 2006055288 | A2 | 5/2006 |
| WO | 2006055780 | A2 | 5/2006 |
| WO | 2006/096262 | A2 | 9/2006 |
| WO | 2007046850 | A2 | 4/2007 |
| WO | 2008005618 | A2 | 1/2008 |
| WO | 2008033983 | A1 | 3/2008 |
| WO | 2008092029 | A2 | 7/2008 |
| WO | 2008/107869 | A1 | 9/2008 |
| WO | 2008/131300 | A2 | 10/2008 |
| WO | 2008131289 | A2 | 10/2008 |
| WO | 2008133808 | A1 | 11/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2022/120068 | A1 | 6/2022 |
| WO | 2022/133138 | A2 | 6/2022 |
| WO | 2023069600 | A1 | 4/2023 |
| WO | 2023069726 | A1 | 4/2023 |

OTHER PUBLICATIONS

PCT/US2020/057202 filed Oct. 23, 2020 International Search Report and Written Opinion dated Jan. 21, 2021.
PCT/US2021/022208 filed Mar. 12, 2021 International Search Report and Written Opinion dated Sep. 3, 2021.
PCT/US2023/014295 filed Mar. 1, 2023 International Search Report and Written Opinion dated Jun. 23, 2023.
U.S. Appl. No. 17/079,320, filed Oct. 23, 2020 Non-Final Office Action dated Jul. 28, 2023.
U.S. Appl. No. 17/200,566, filed Mar. 12, 2021 Restriction Requirement dated Jul. 14, 2023.
PCT/US2021/061638 filed Dec. 2, 2021 International Search Report and Written Opinion dated Apr. 12, 2022.
PCT/US2021/063903 filed Dec. 16, 2021, International Search Report and Written Opinion dated Jun. 28, 2022.
PCT/US2022/047252 filed Oct. 20, 2022 International Search Report and Written Opinion dated Mar. 21, 2023.
PCT/US2022/047444 filed Oct. 21, 2022 International Search Report and Written Opinion dated Mar. 7, 2023.
U.S. Appl. No. 17/079,320, filed Oct. 23, 2020 Restriction Requirement dated Mar. 29, 2023.
PCT/US2021/022226 filed Mar. 12, 2021 International Search Report and Written Opinion dated Oct. 21, 2021.
U.S. Appl. No. 17/200,566, filed Mar. 12, 2021 Final Office Action dated Dec. 28, 2023.
U.S. Appl. No. 17/200,566, filed Mar. 12, 2021 Non-Final Office Action dated Oct. 6, 2023.
Strittmatter, F., Eisel, M., Brinkmann, R., Cordes, J., Lange, B., & Sroka, R., "Laser Induced Lithotripsy: a Review, insight into laboratory work, and lessons learned." Translational Biophotonics, 2(1-2), e201900029. (2020).
Traxer, O., & Keller, E. X., "Thulium fiber laser: the new player for kidney stone treatment? A comparison with Holmium: YAG laser." World Journal of Urology, 38, 1883-1894. (2020).
U.S. Appl. No. 17/079,320, filed Oct. 23, 2020 Advisory Action dated Apr. 11, 2024.
U.S. Appl. No. 17/079,320, filed Oct. 23, 2020 Final Office Action dated Jan. 18, 2024.
U.S. Appl. No. 17/079,320, filed Oct. 23, 2020 Non-Final Office Action dated May 7, 2024.
U.S. Appl. No. 17/200,566, filed Mar. 12, 2021 Notice of Allowance dated Apr. 3, 2024.

* cited by examiner

GUIDEWIRE-MANAGEMENT DEVICES AND METHODS THEREOF

PRIORITY

This application claims the benefit of priority to U.S. Provisional Application No. 62/989,397, filed Mar. 13, 2020, which is incorporated by reference in its entirety into this application.

BACKGROUND

A catheter is typically placed in a blood vessel of a patient using the Seldinger technique, which involves inserting a hollow needle into the blood vessel, inserting a guidewire into the needle, advancing the guidewire into the blood vessel, and removing the needle from the blood vessel leaving the guidewire in place. The catheter is then advanced over the guidewire until it is suitably placed with the patient's vasculature. The guidewire is then removed from the patient.

Guidewires for use in accordance with the Seldinger technique are typically packaged in a coiled-tube dispenser to keep the guidewires sterile and make handling the guidewires less cumbersome. However, inserting such a guidewire from a dispenser into a hollow needle requires two hands. In particular, one hand is required to hold both the needle and an engagement piece configured to guide the guidewire into the needle, while another hand is required to grip the guidewire and direct the guidewire from the dispenser into the needle. The more the guidewire is handled, the more opportunity for contamination or damage to the guidewire. In view of the foregoing, there is a need for better guidewire management in medical procedures such as those requiring the Seldinger technique.

Disclosed herein are guidewire-management devices and methods thereof that address the foregoing.

SUMMARY

Disclosed herein is method of a guidewire-management device including, in some embodiments, a connecting step of connecting a first sleeve of the guidewire-management device to a hub of a medical device inserted into an insertion site of a patient. The first sleeve is configured as a male connector with a Luer taper. The method further includes an advancing step of advancing a guidewire of the guidewire-management device from the first sleeve through the hub of the medical device and into the insertion site of the patient. The guidewire is disposed within a sterile barrier configured to maintain sterility of the guidewire until being fed into the first sleeve. The method further includes a withdrawing step of withdrawing the guidewire from the insertion site of the patient through the hub of the medical device and into the first sleeve. A bore in a proximal portion of the first sleeve includes a metering-mechanism configured to meter the sterile barrier out of the bore to recover the guidewire when withdrawing the guidewire from the insertion site of the patient In some embodiments, the advancing step includes pinching the guidewire within the sterile barrier and advancing the guidewire into the first sleeve by hand. The sterile barrier is a pleated bag or a bellowed boot.

In some embodiments, the advancing step includes pressing the guidewire within the sterile barrier onto a thumb wheel and rolling the thumb wheel to advance the guidewire into the first sleeve, the sterile barrier being a pleated bag.

In some embodiments, the method further includes a ceasing step of ceasing to advance the guidewire into the insertion site of the patient when a ball end of a proximal portion of the guidewire is captured in a constriction of a bore in a proximal portion of a second sleeve of the guidewire-management device.

In some embodiments, a seal in the first sleeve blocks fluid from entering or escaping the guidewire-management device when withdrawing the guidewire from the insertion site of the patient through the hub of the medical device and into the first sleeve.

In some embodiments, a distal portion of the guidewire includes a 'J'-shaped tip configured to straighten as the tip of the guidewire enters the first sleeve when withdrawing the guidewire from the insertion site.

In some embodiments, the method further includes ceasing to withdraw the guidewire from the insertion site of the patient when a proximal end of the guidewire abuts a plug in a proximal portion of a guidewire conduit of the guidewire-management device.

Also disclosed herein is a guidewire-management device including, in some embodiments, a handle, a guidewire, a first sleeve formed in a distal portion of the handle, a second sleeve formed in a proximal portion of the handle, a wheel disposed under the guidewire between the first sleeve and the second sleeve configured to grip the guidewire when the wheel is turned, and a knob coupled to the wheel. The guidewire extends between the first sleeve and the second sleeve disposed within a capsule to maintain sterility of the guidewire. The knob is configured to assist in distally feeding the guidewire out of the guidewire-management device by way of the first sleeve when the knob is rotated clockwise. The knob is also configured to assist in proximally feeding the guidewire into the guidewire-management device by way of the first sleeve when the knob is rotated counterclockwise.

In some embodiments, the first sleeve has a distal portion configured as a male connector with a Luer taper for connecting the first sleeve to a complementary female connector.

In some embodiments, the first sleeve is configured to straighten a 'J'-shaped tip in a distal portion of the guidewire as the tip of the guidewire enters the first sleeve when proximally feeding the guidewire into the guidewire-management device.

In some embodiments, the second sleeve has a proximal portion including a bore with a constriction configured to capture a ball end of the guidewire and stop the guidewire from completely passing through the second sleeve.

In some embodiments, the guidewire-management device further includes a guidewire conduit coupled to the second sleeve. The guidewire conduit is configured to distally feed the guidewire into the guidewire-management device by way of the second sleeve. The guidewire conduit is configured to maintain sterility of the guidewire outside of the first sleeve, the capsule, and the second sleeve.

In some embodiments, the handle includes a channel configured to hold the guidewire conduit therein when the guidewire conduit is in a coiled configuration.

Also disclosed herein is a guidewire-management device including, in some embodiments, a handle, a guidewire, a first sleeve formed in a distal portion of the handle, a second sleeve formed in a proximal portion of the handle, and a gapped guidewire conduit coupled to the second sleeve. At least a length of the guidewire extends between the first sleeve and the second sleeve disposed within a sterile barrier configured to maintain sterility of the guidewire. A gap in the gapped guidewire conduit is configured to allow the guidewire to be grasped and distally fed into the guidewire-management device by way of the second sleeve.

In some embodiments, the first sleeve has a distal portion configured as a male connector with a Luer taper for connecting the first sleeve to a complementary female connector.

In some embodiments, the first sleeve is configured to straighten a 'J'-shaped tip in a distal portion of the guidewire as the tip of the guidewire enters the first sleeve when proximally feeding the guidewire into the guidewire-management device.

In some embodiments, the second sleeve has a proximal portion including a bore with a constriction configured to capture a ball end of the guidewire and stop the guidewire from completely passing through the second sleeve.

In some embodiments, the sterile barrier is a pleated bag over an entirety of the guidewire excepting that within or distal to the first sleeve. The bag is configured to pleat as the bag is inserted into a bore in a proximal portion of the first sleeve while distally feeding the guidewire out of the guidewire-management device.

In some embodiments, the sterile barrier is a splittable casing over an entirety of the guidewire excepting that within or distal to the first sleeve. The splittable casing is configured to split off the guidewire while distally feeding the guidewire out of the guidewire-management device.

In some embodiments, the guidewire-management device further includes a first split sleeve in the distal portion of the handle. The first split sleeve is configured to discharge the splittable casing while distally feeding the guidewire out of the guidewire-management device.

Also disclosed herein is a guidewire-management device including, in some embodiments, a handle, a guidewire, a first sleeve formed in a distal portion of the handle, a second sleeve formed in a proximal portion of the handle, a guidewire conduit coupled to the second sleeve, and a tether coupled to a proximal portion of the guidewire and disposed in the guidewire conduit along with the guidewire. The guidewire extends between the first sleeve and the second sleeve optionally disposed within a capsule to maintain sterility of the guidewire. The guidewire conduit is configured to distally feed the guidewire into the guidewire-management device by way of the second sleeve. The guidewire conduit is configured to maintain sterility of the guidewire outside of the first sleeve, the capsule, and the second sleeve. The tether is configured to assist in distally feeding the guidewire out of the guidewire-management device by way of the first sleeve when the tether is pulled away from the guidewire-management device.

In some embodiments, the first sleeve has a distal portion configured as a male connector with a Luer taper for connecting the first sleeve to a complementary female connector.

In some embodiments, the first sleeve is configured to straighten a 'J'-shaped tip in a distal portion of the guidewire as the tip of the guidewire enters the first sleeve when proximally feeding the guidewire into the guidewire-management device.

In some embodiments, the second sleeve has a proximal portion including a bore with a constriction configured to capture a mass about a proximal portion of the guidewire and stop the guidewire from completely passing through the second sleeve.

In some embodiments, the handle includes a guidewire-conduit channel configured to hold the guidewire conduit therein when the guidewire conduit is in a coiled configuration.

In some embodiments, the handle includes a tether channel extending through a portion of the handle. The tether is disposed in the tether channel without the guidewire.

In some embodiments, the tether wire has a stiffness sufficient for proximally feeding the tether wire into the guidewire-management device along with the guidewire.

In some embodiments, the guidewire-management device further includes a thumb wheel configured to assist in distally feeding the tether wire out of the guidewire-management device.

In some embodiments, the tether wire is coupled to a slider disposed in a slot of the handle. The slider configured to provide a user interface for at least distally feeding the guidewire out of the guidewire-management device.

In some embodiments, the guidewire-management device is configured such that the tether wire never contacts the guidewire except for a coupling that couples proximal ends of the tether wire and the guidewire together.

In some embodiments, the guidewire is disposed in a splittable casing in at least the guidewire conduit. Any portion of the splittable casing that splits off of the guidewire forms a tether line configured to provide a user interface for at least distally feeding the guidewire out of the guidewire-management device.

Also disclosed herein is a guidewire-management device including, in some embodiments, a handle, a guidewire, a first sleeve formed in a distal portion of the handle, a second sleeve formed in a proximal portion of the handle, a guidewire conduit coupled to the second sleeve, and a combination of a thumb wheel, a guidewire-gripping wheel coupled to the thumb wheel, and a compression wheel between the first sleeve and the second sleeve. The guidewire is concealed in the handle between the first sleeve and the second sleeve to maintain sterility of the guidewire. The guidewire conduit is configured to distally feed the guidewire into the guidewire-management device by way of the second sleeve, as well as maintain the sterility of the guidewire in combination with the handle. The guidewire is disposed between the guidewire-gripping wheel and the compression wheel such that the guidewire is distally fed out of the guidewire-management device by way of the first sleeve or proximally fed into the guidewire-management device by way of the first sleeve in accordance with turning the thumb wheel.

These and other features of the concepts provided herein will become more apparent to those of skill in the art in view of the accompanying drawings and following description, which describe particular embodiments of such concepts in greater detail. In addition, U.S. patent application Ser. No. 17/079,320, filed Oct. 23, 2020, is incorporated by reference in its entirety into this application.

DRAWINGS

FIG. 1 provides an isometric view of a first guidewire-management device in accordance with some embodiments.

Figure 2:
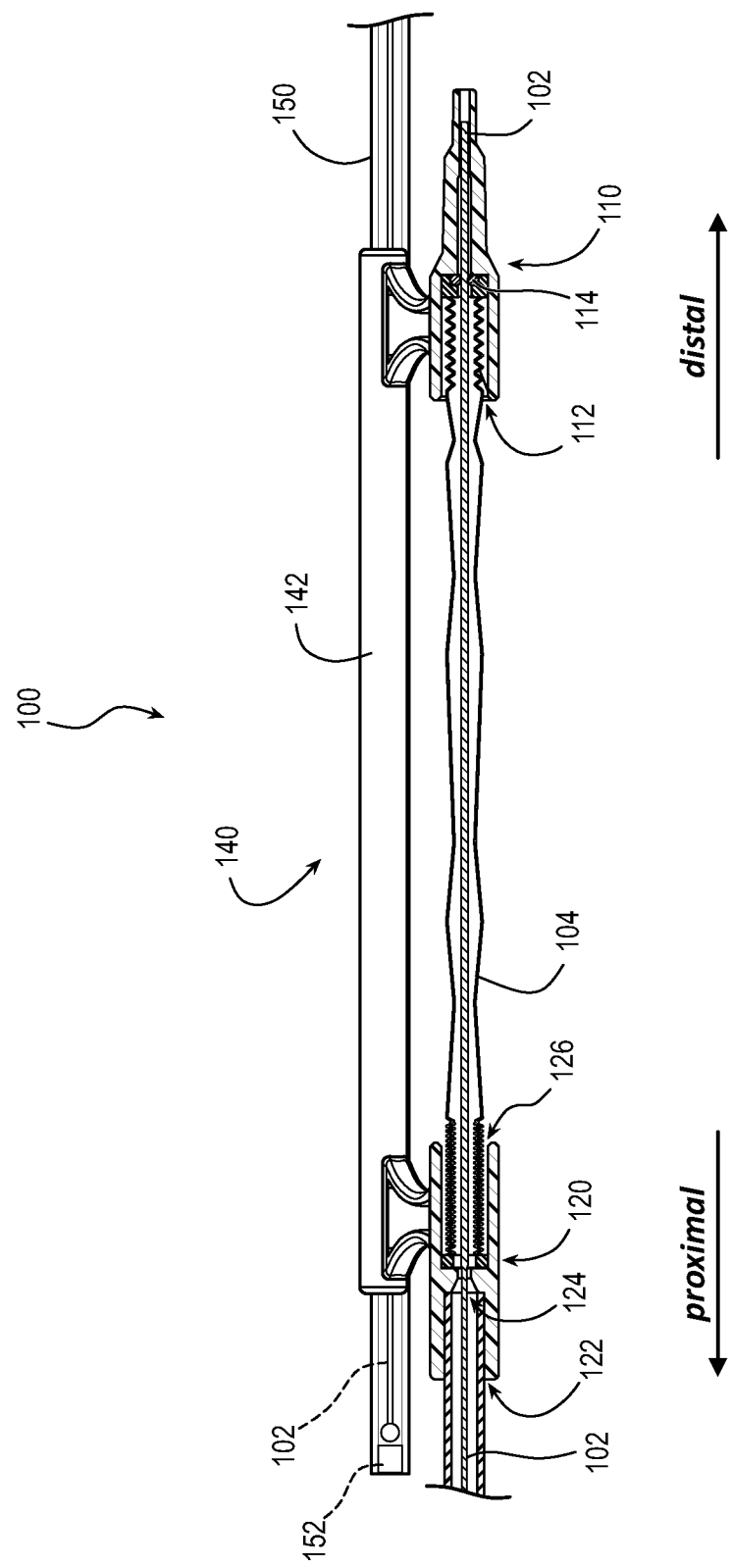

FIG. 2 provides a longitudinal cross section of the first guidewire-management device in accordance with some embodiments.

Figure 3:
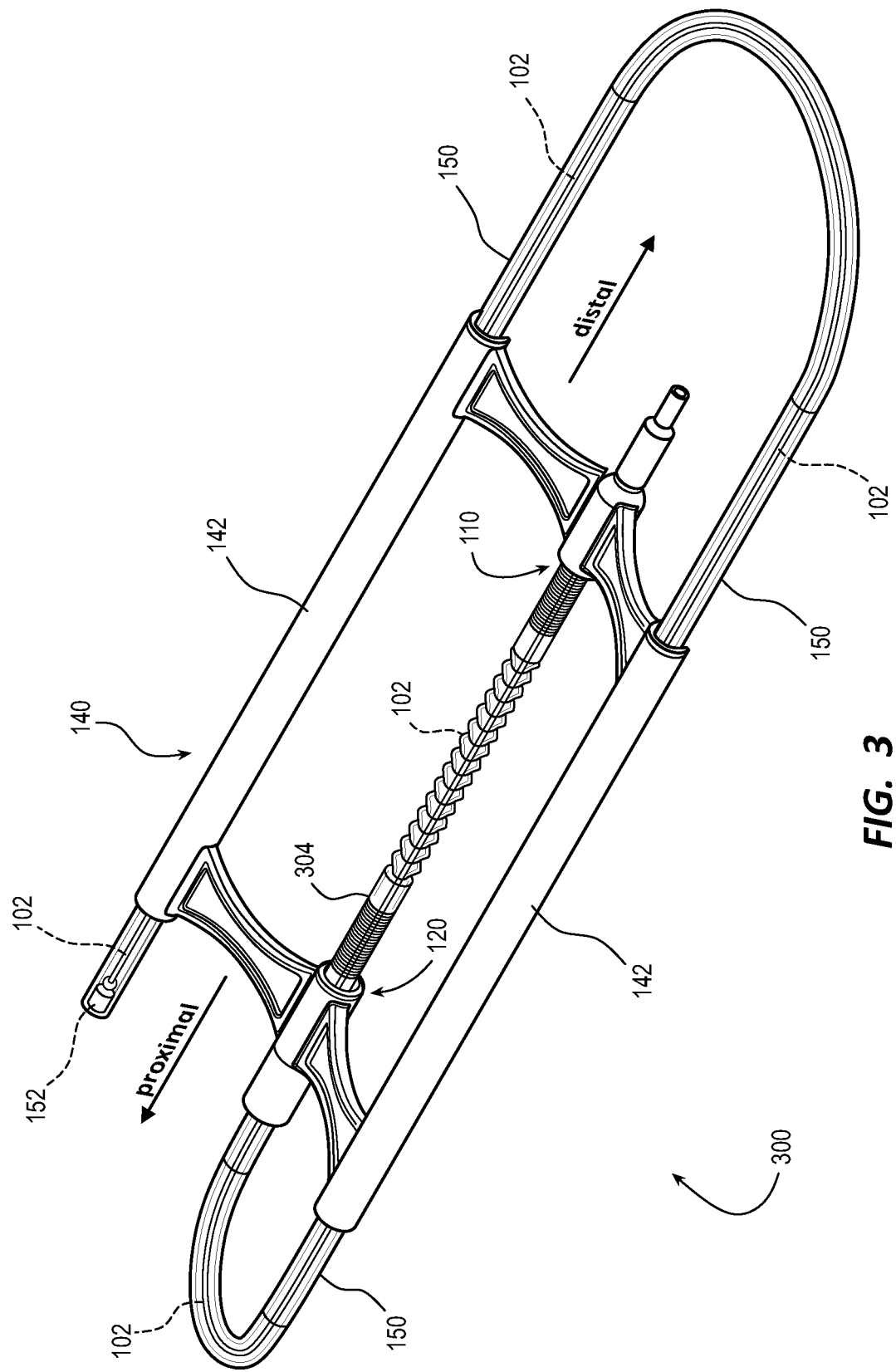

FIG. 3 provides an isometric view of a second guidewire-management device in accordance with some embodiments.

Figure 4:
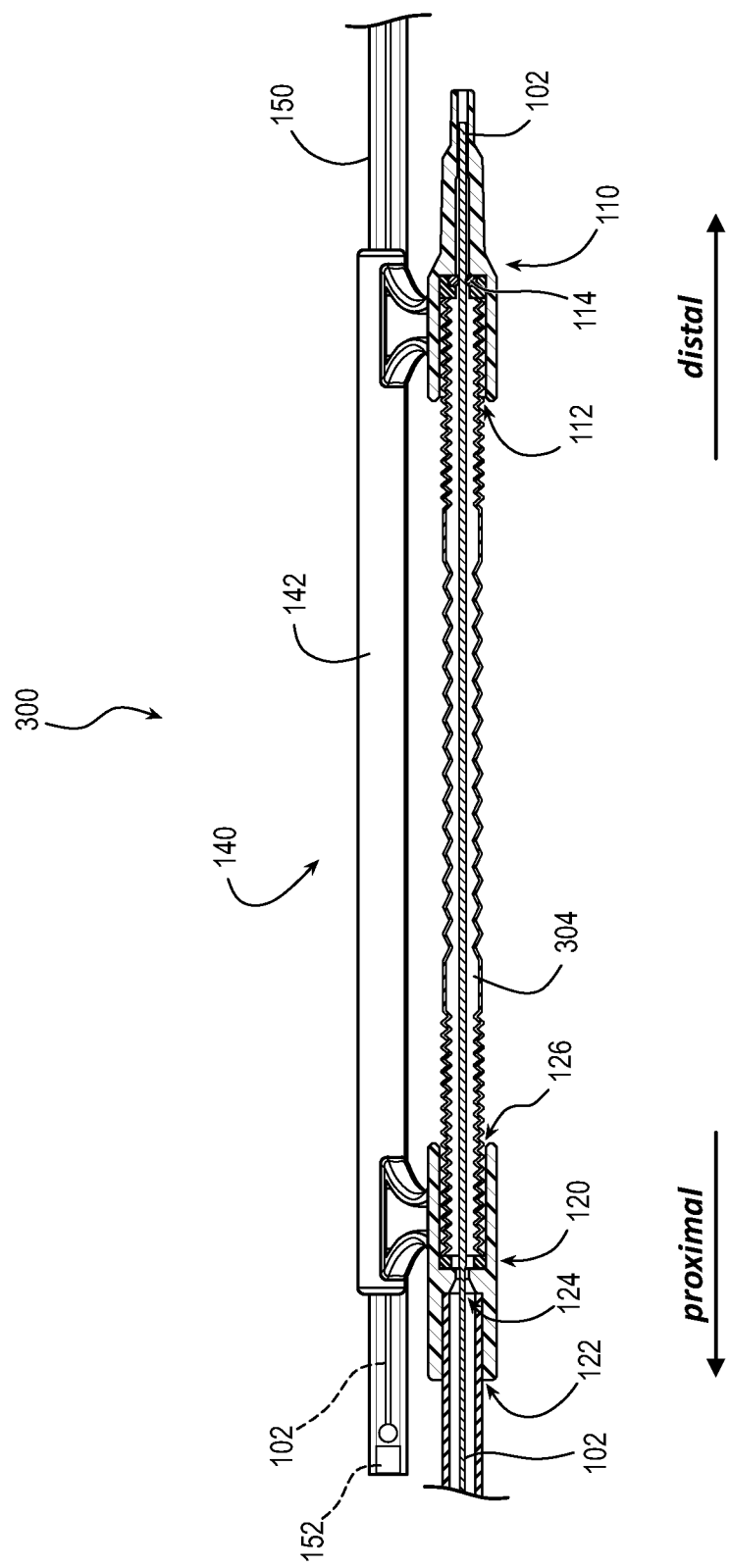

FIG. 4 provides a longitudinal cross section of the second guidewire-management device in accordance with some embodiments.

Figure 5:
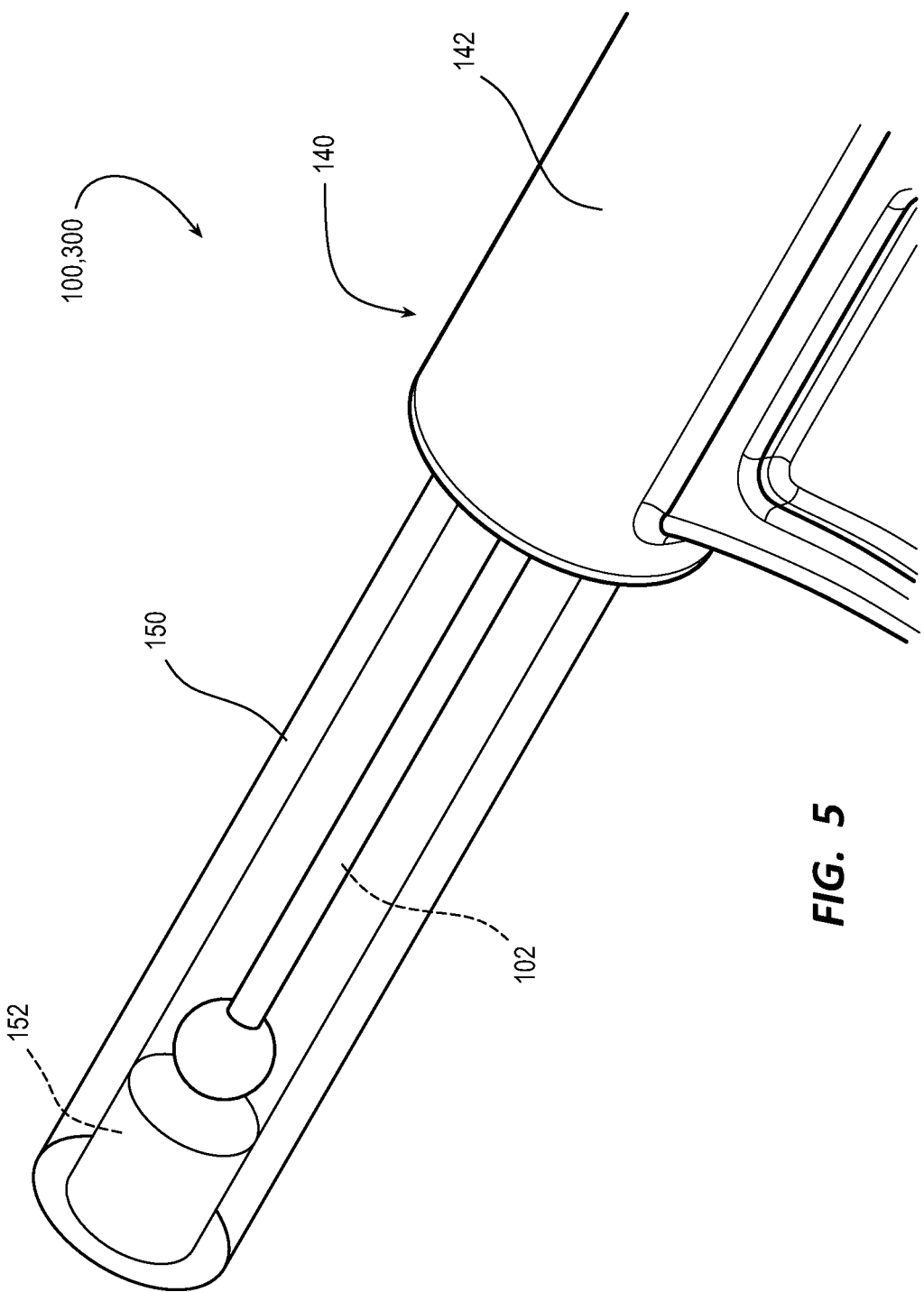

FIG. 5 provides a detailed view of a ball end of a guidewire distal to a plug in a guidewire conduit in accordance with some embodiments.

Figure 6:
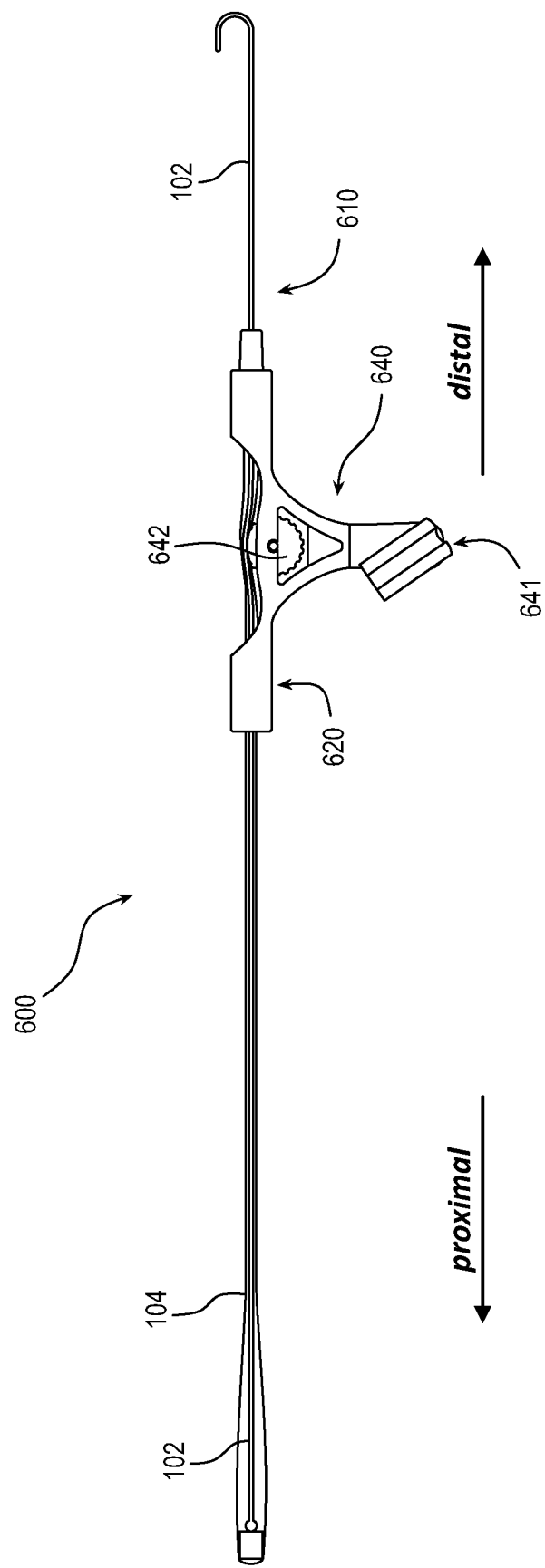

FIG. 6 provides a side view of a third guidewire-management device in accordance with some embodiments.

Figure 7:
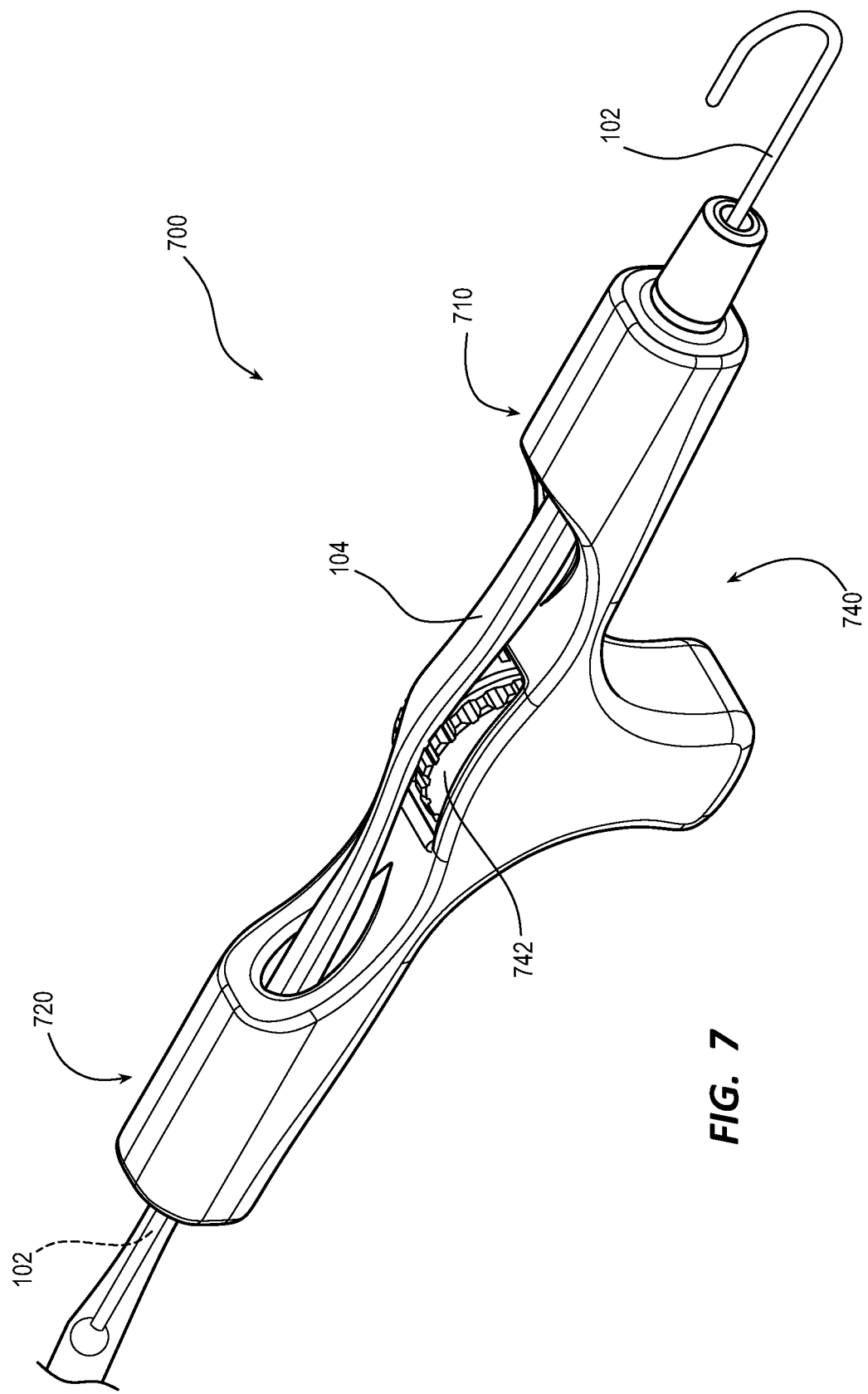

FIG. 7 provides an isometric view of a handle of a fourth guidewire-management device in accordance with some embodiments.

Figure 8:
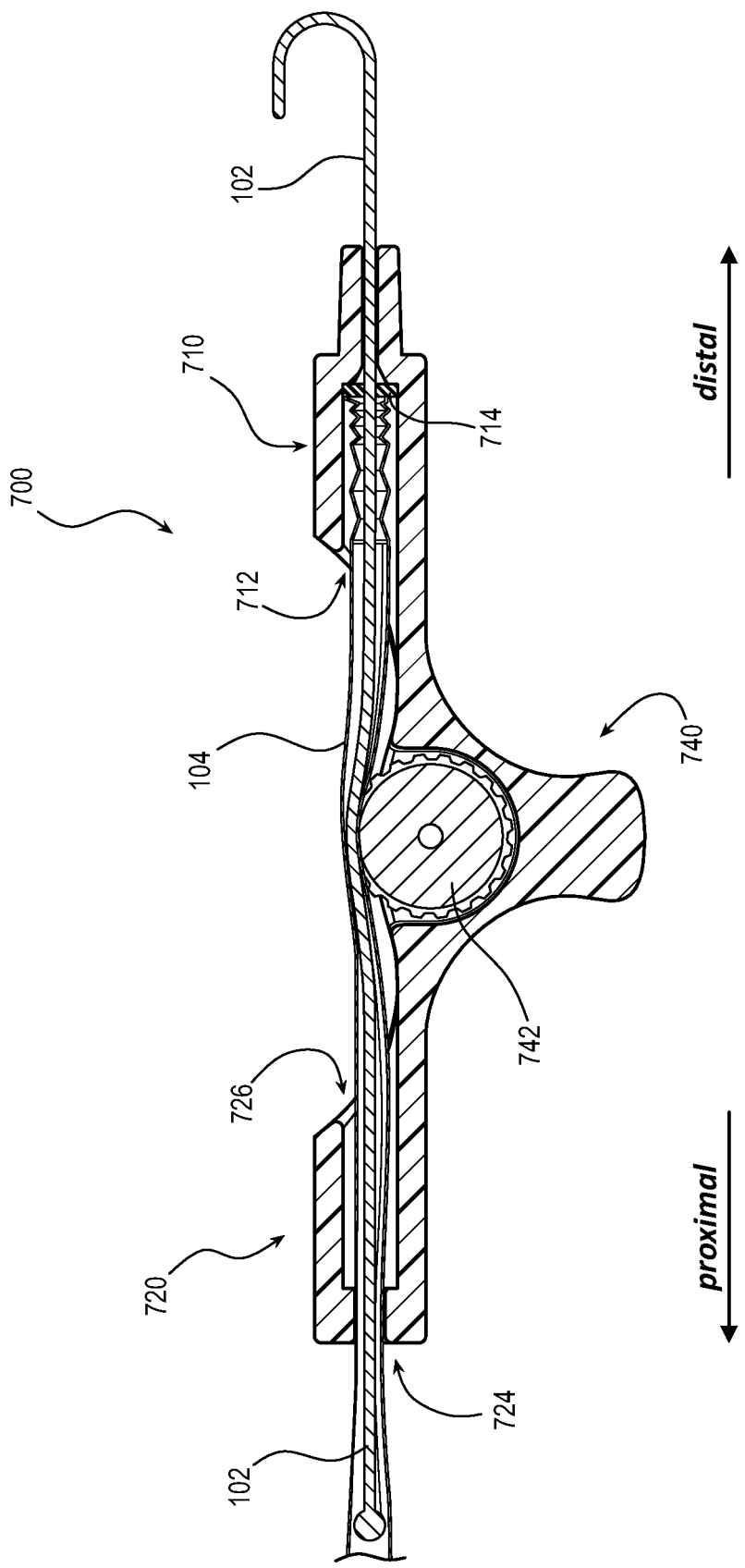

FIG. 8 provides a longitudinal cross section of the fourth guidewire-management device in accordance with some embodiments.

Figure 9:
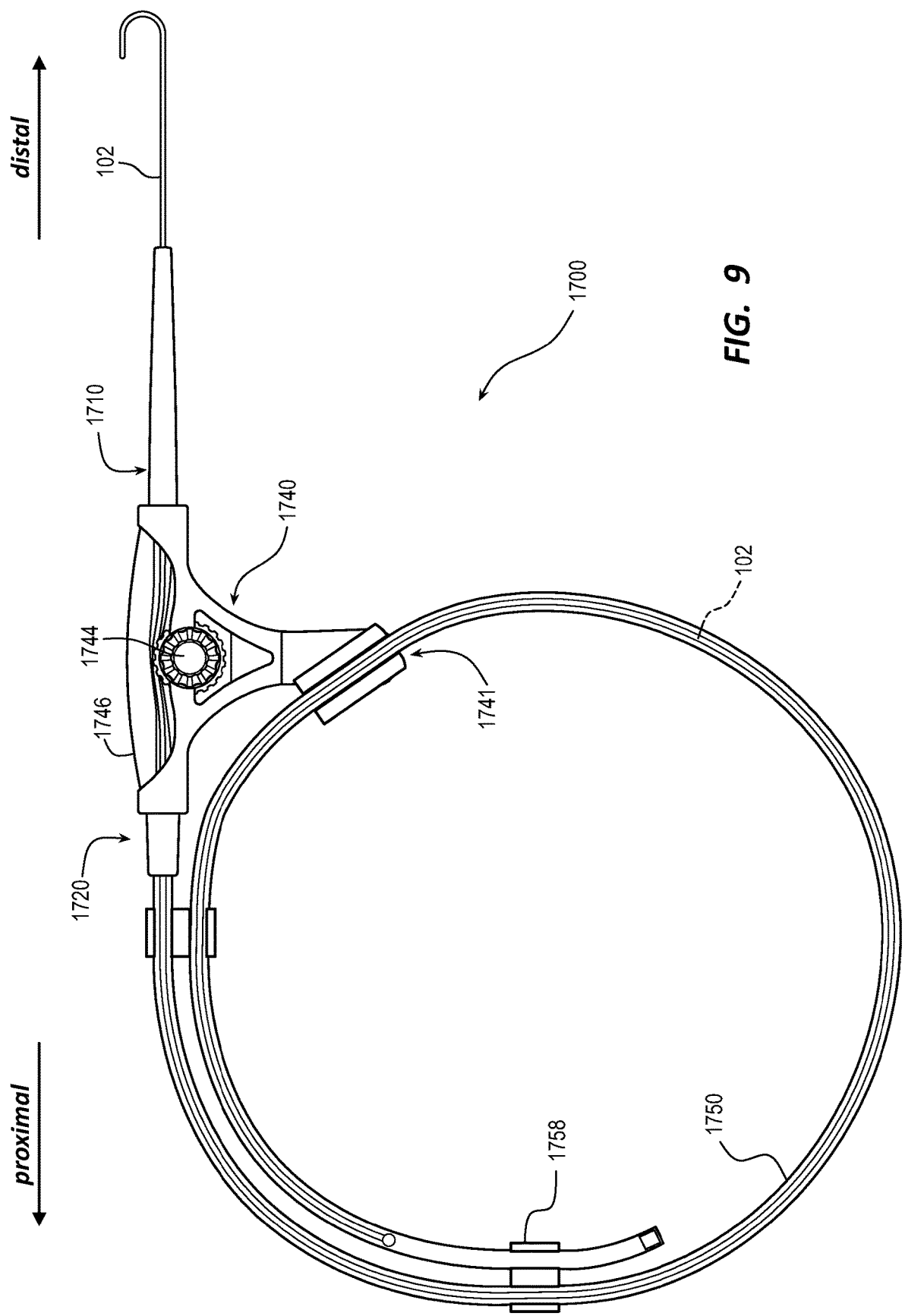

FIG. 9 provides a side view of a fifth guidewire-management device in accordance with some embodiments.

Figure 10:
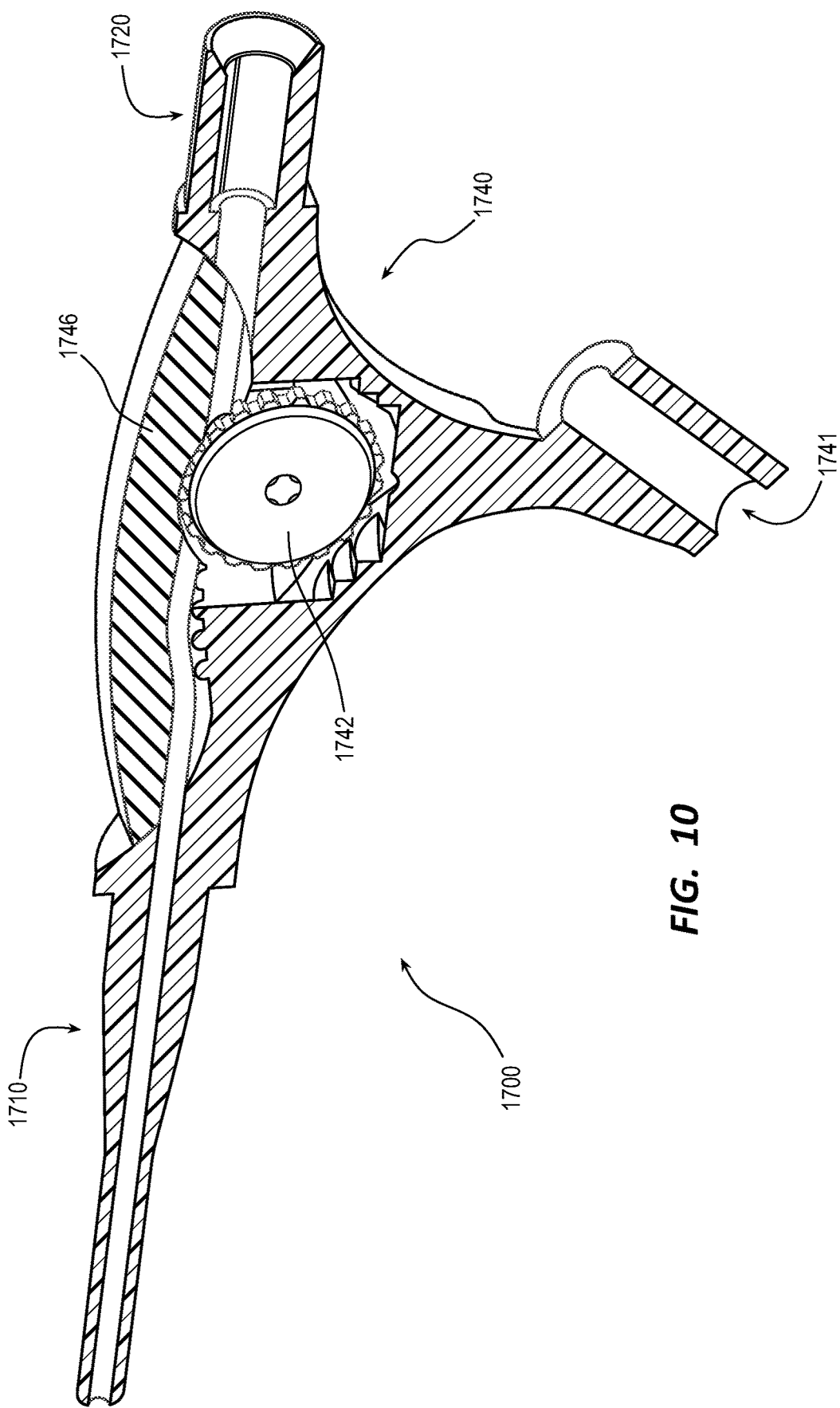

FIG. 10 provides a longitudinal cross section of the fifth guidewire-management device in accordance with some embodiments.

Figure 11:
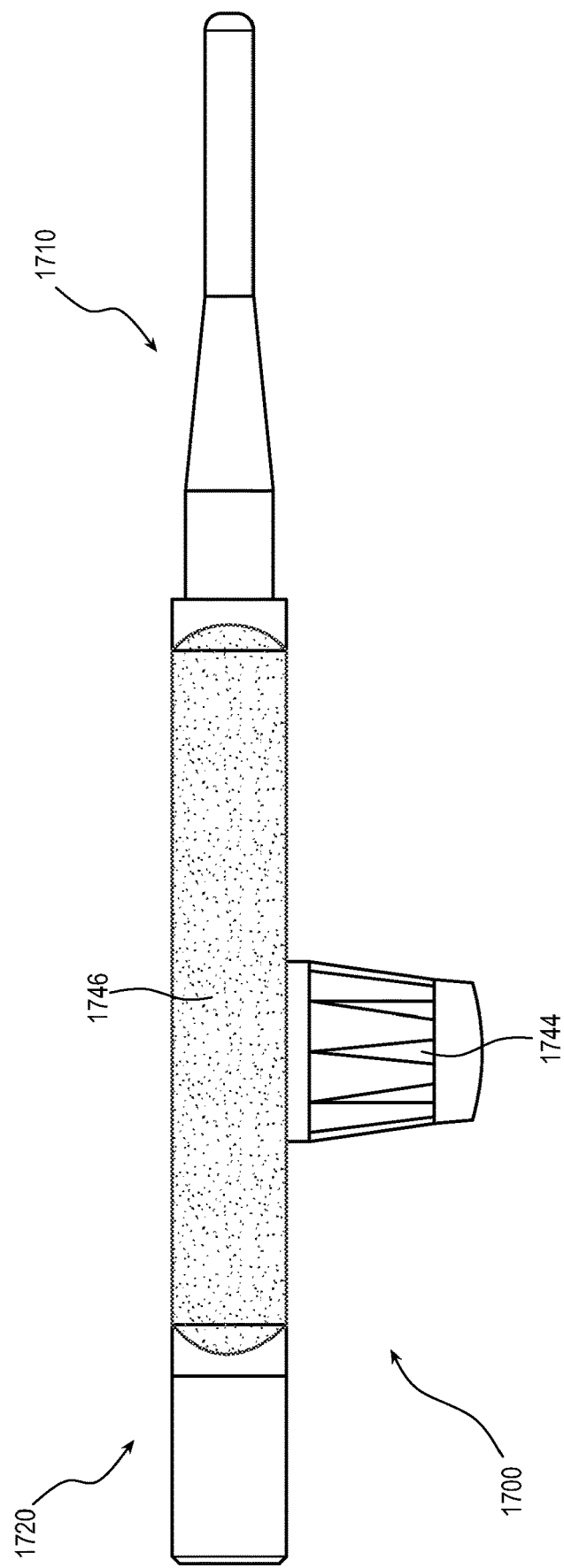

FIG. 11 provides a top view of the sixth guidewire-management device in accordance with some embodiments.

Figure 12:
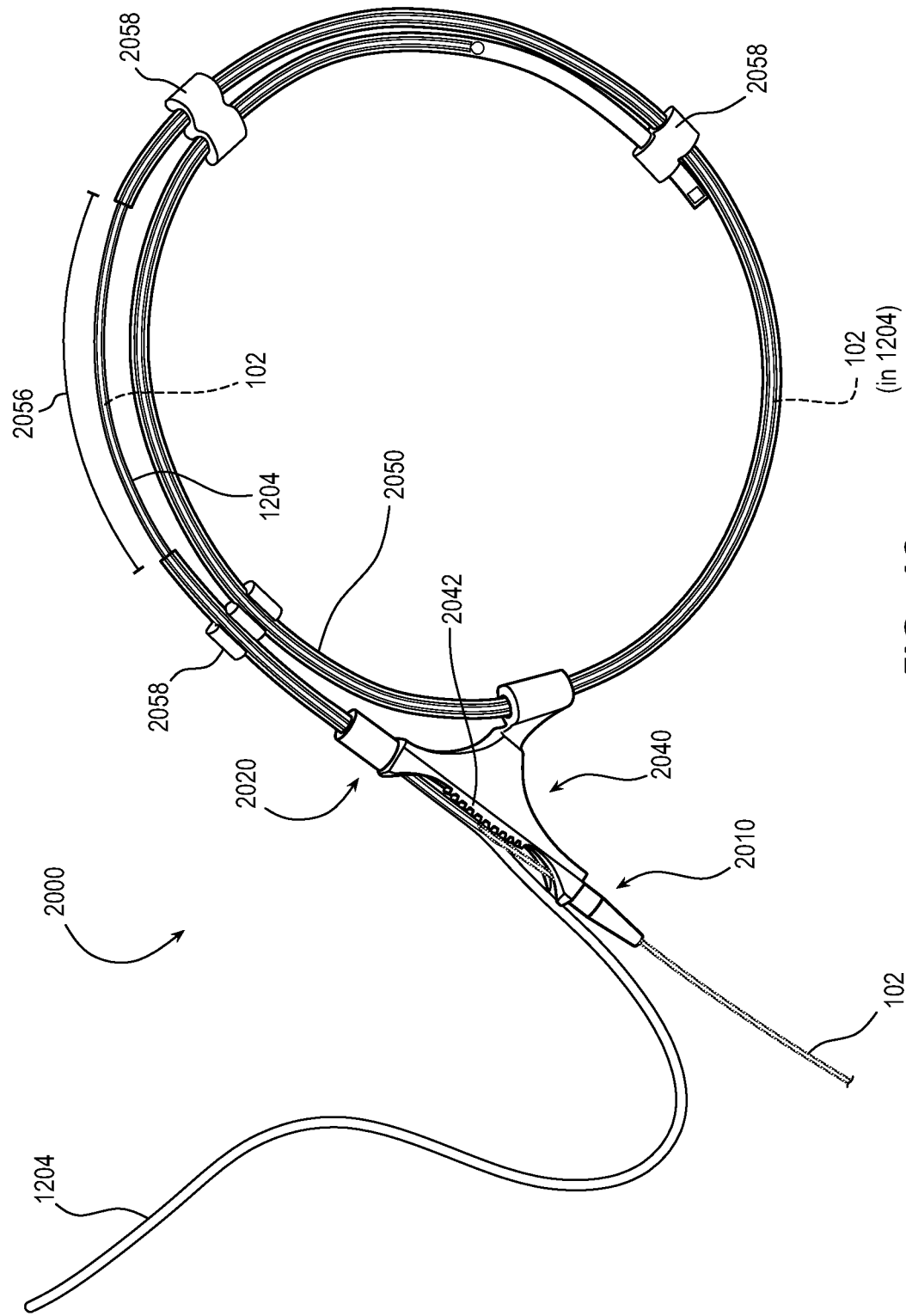

FIG. 12 provides a side view of a seventh guidewire-management device in accordance with some embodiments.

Figure 13:
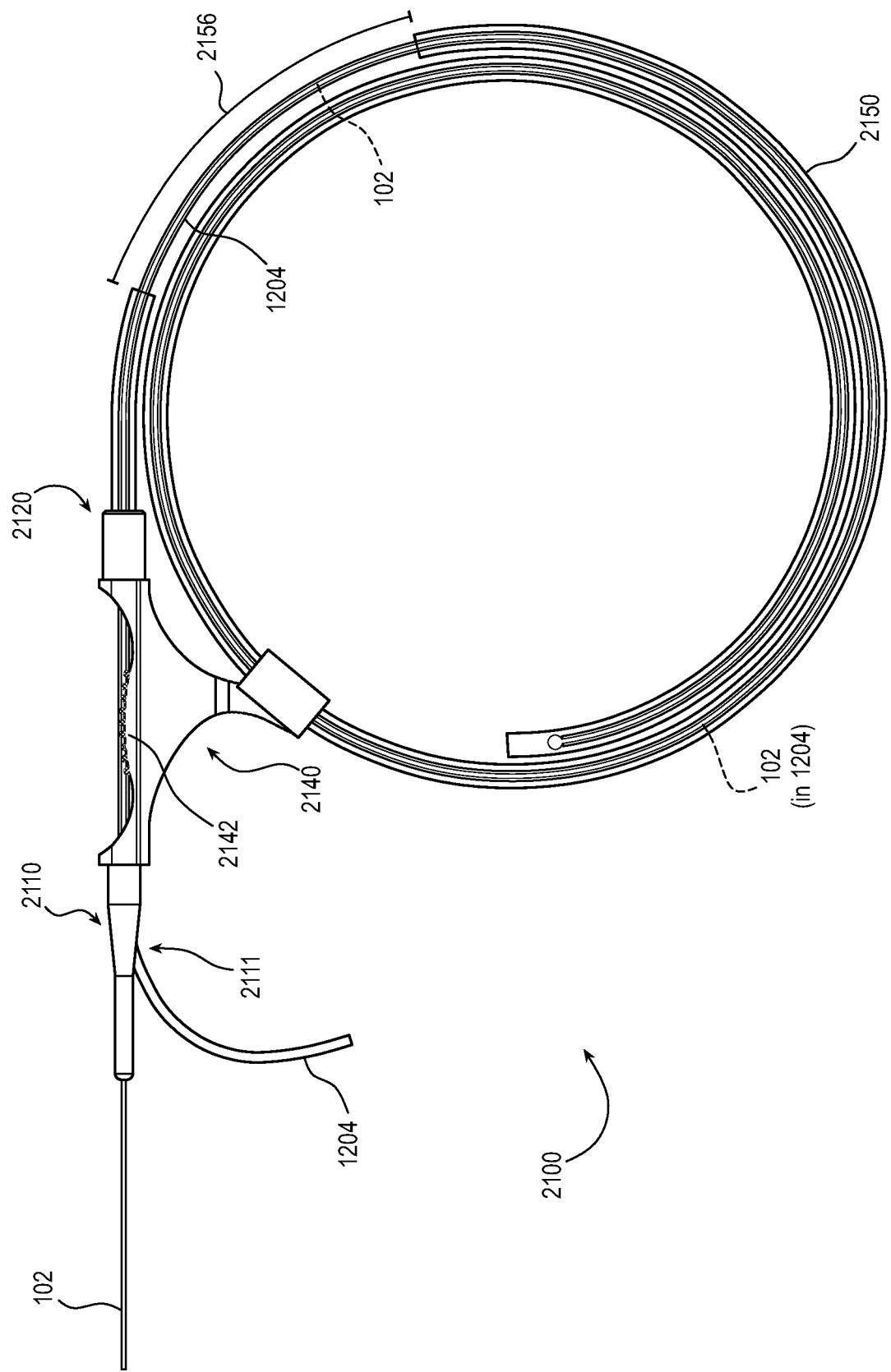

FIG. 13 provides a side view of an eighth guidewire-management device in accordance with some embodiments.

Figure 14:
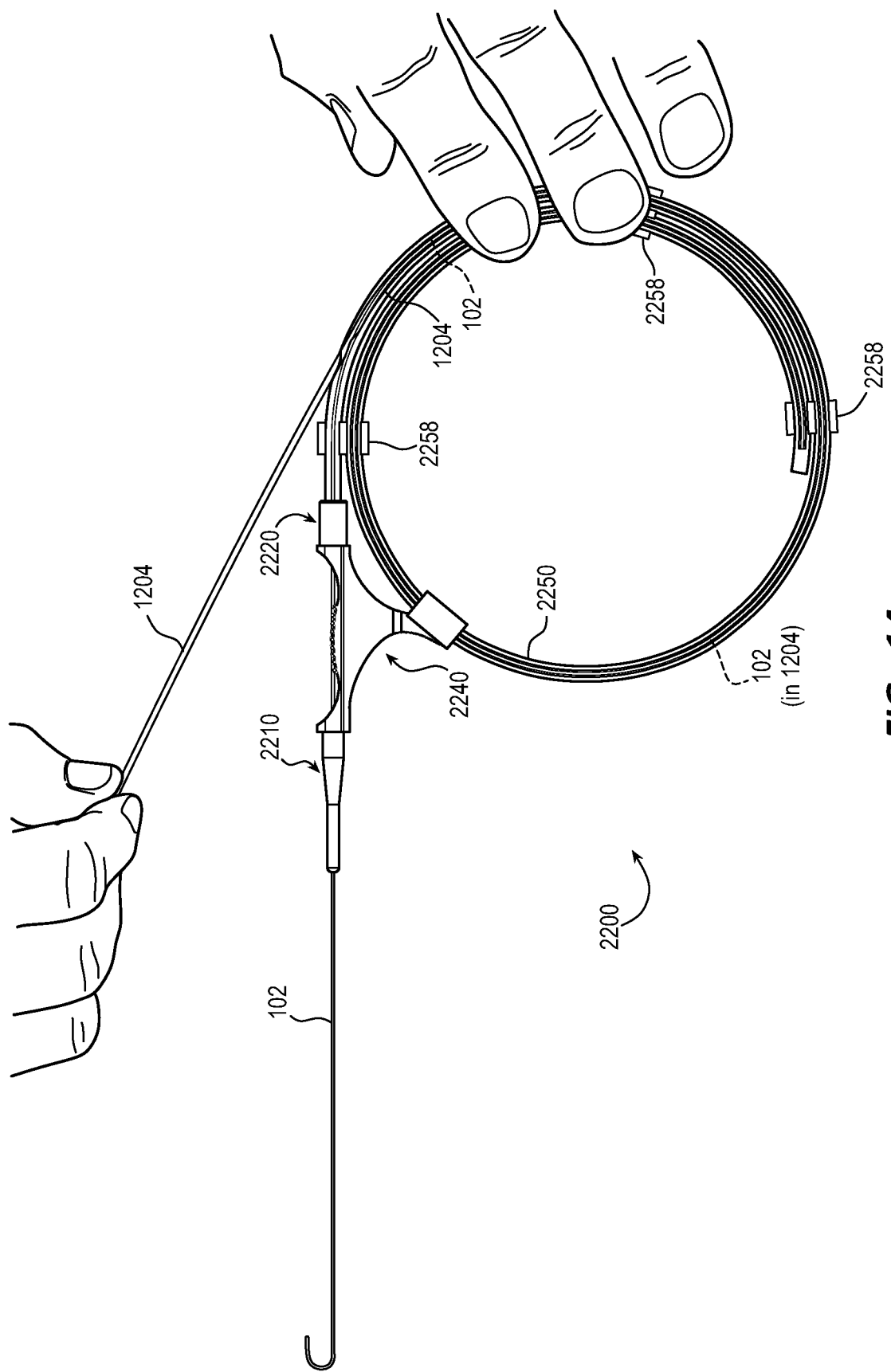

FIG. 14 provides a side view of a ninth guidewire-management device in accordance with some embodiments.

Figure 15:
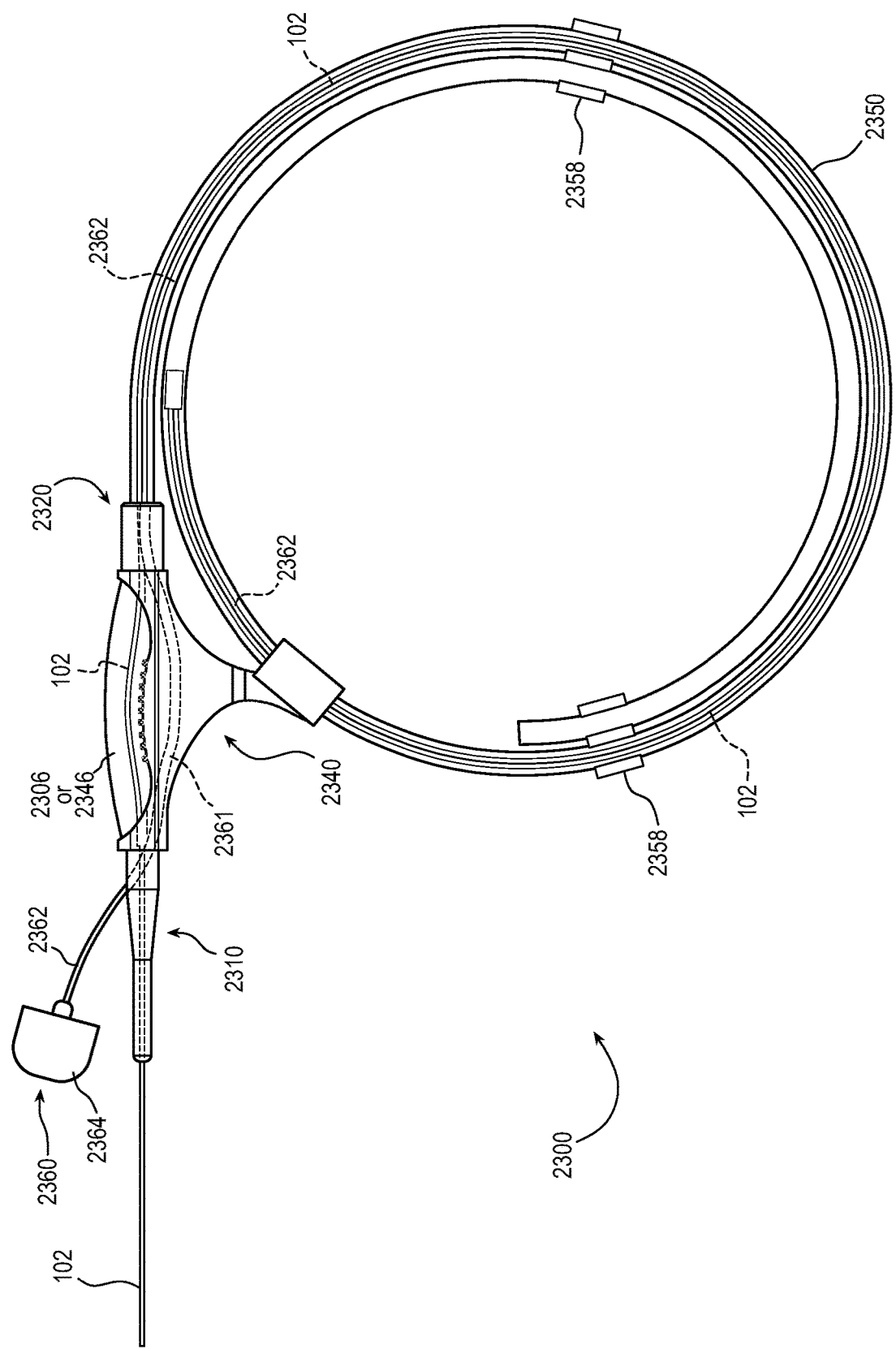

FIG. 15 provides a side view of a tenth guidewire-management device in accordance with some embodiments.

Figure 16:
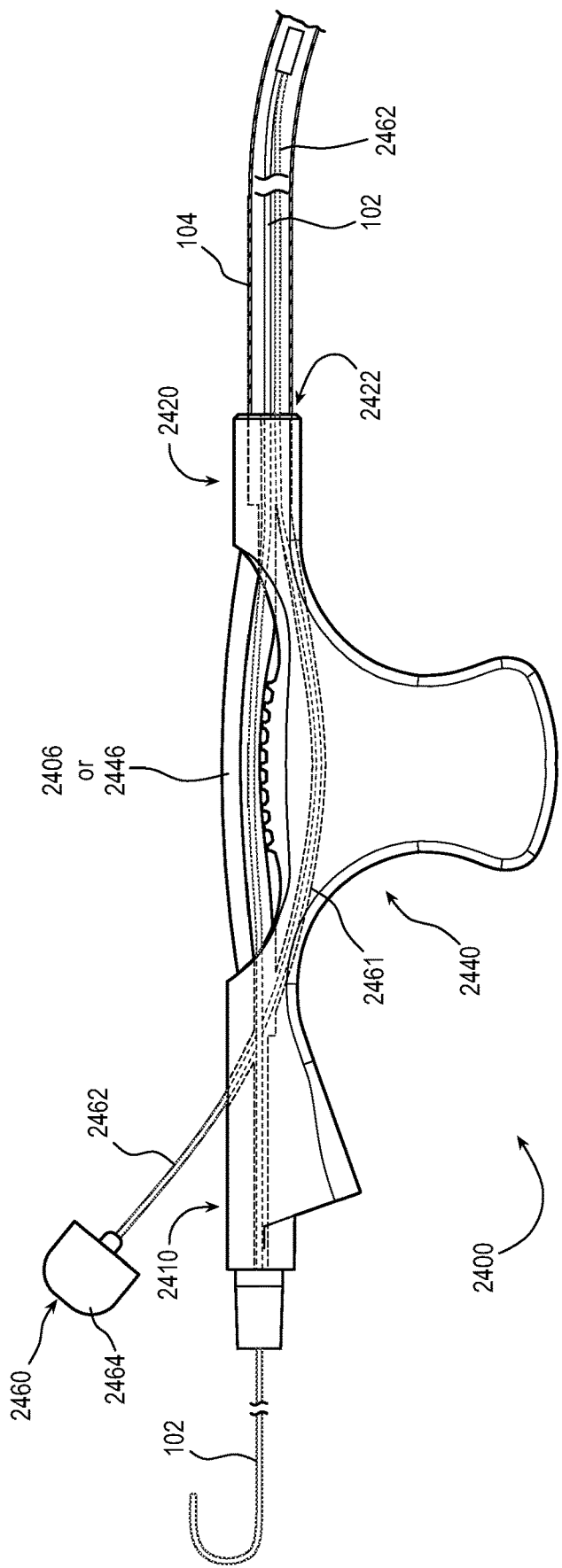

FIG. 16 provides a side view of an eleventh guidewire-management device in accordance with some embodiments.

Figure 17:
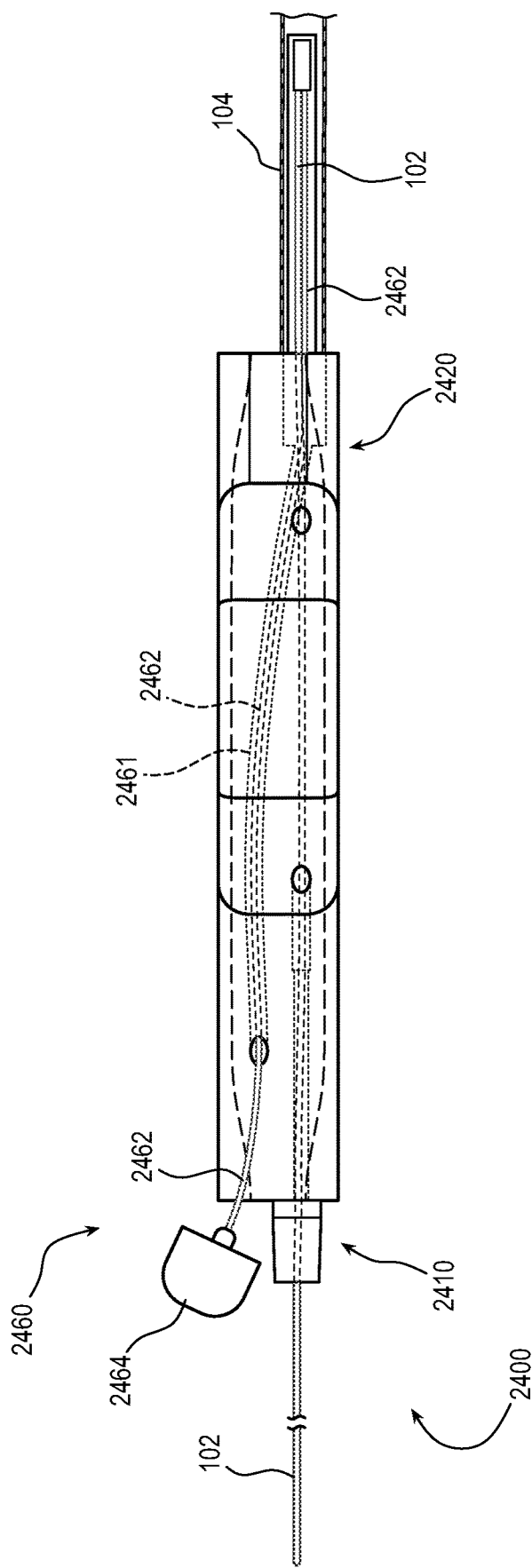

FIG. 17 provides a top view of a handle of the eleventh guidewire-management device in accordance with some embodiments.

Figure 18:
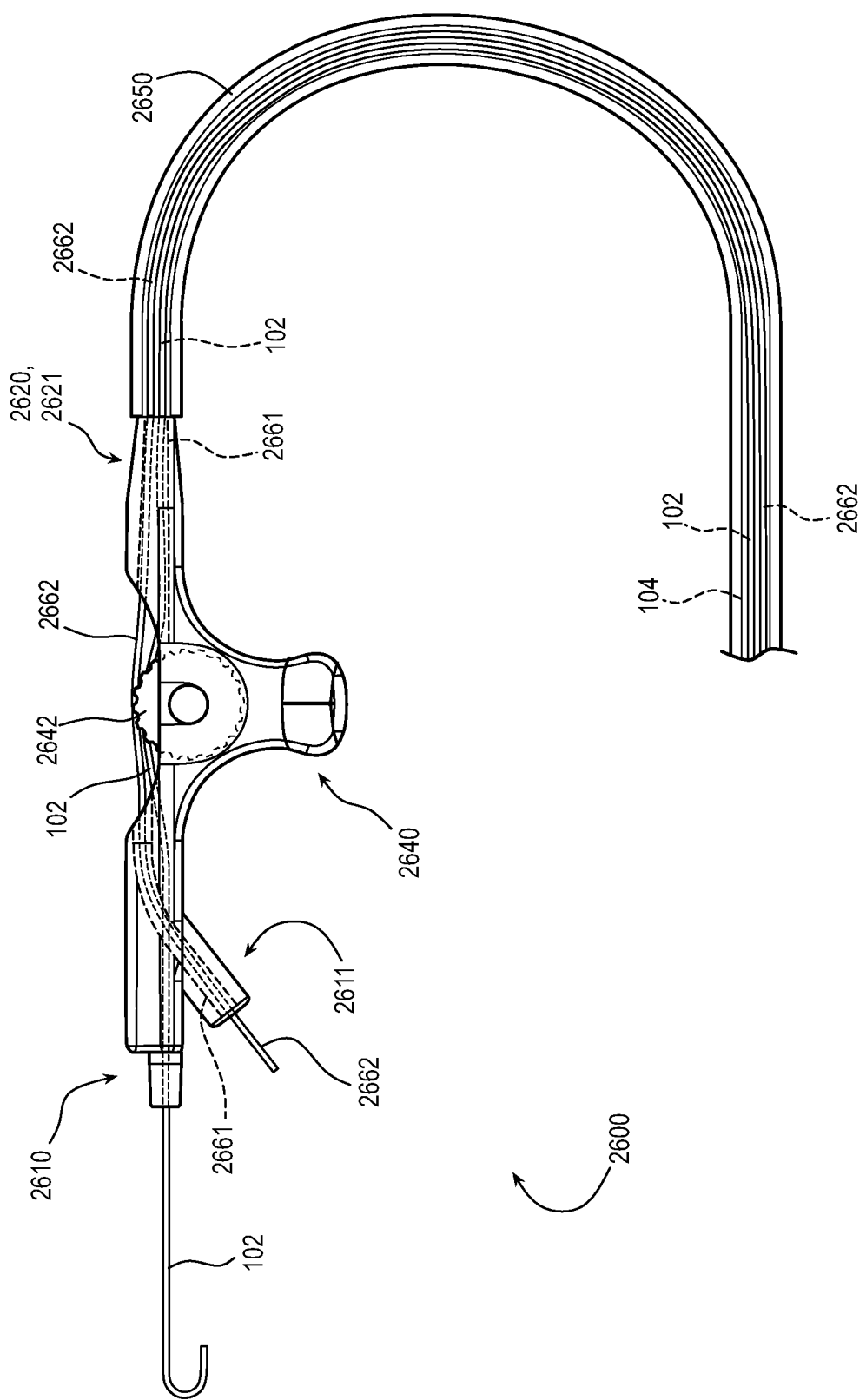

FIG. 18 provides a side view of a twelfth guidewire-management device in accordance with some embodiments.

Figure 19:
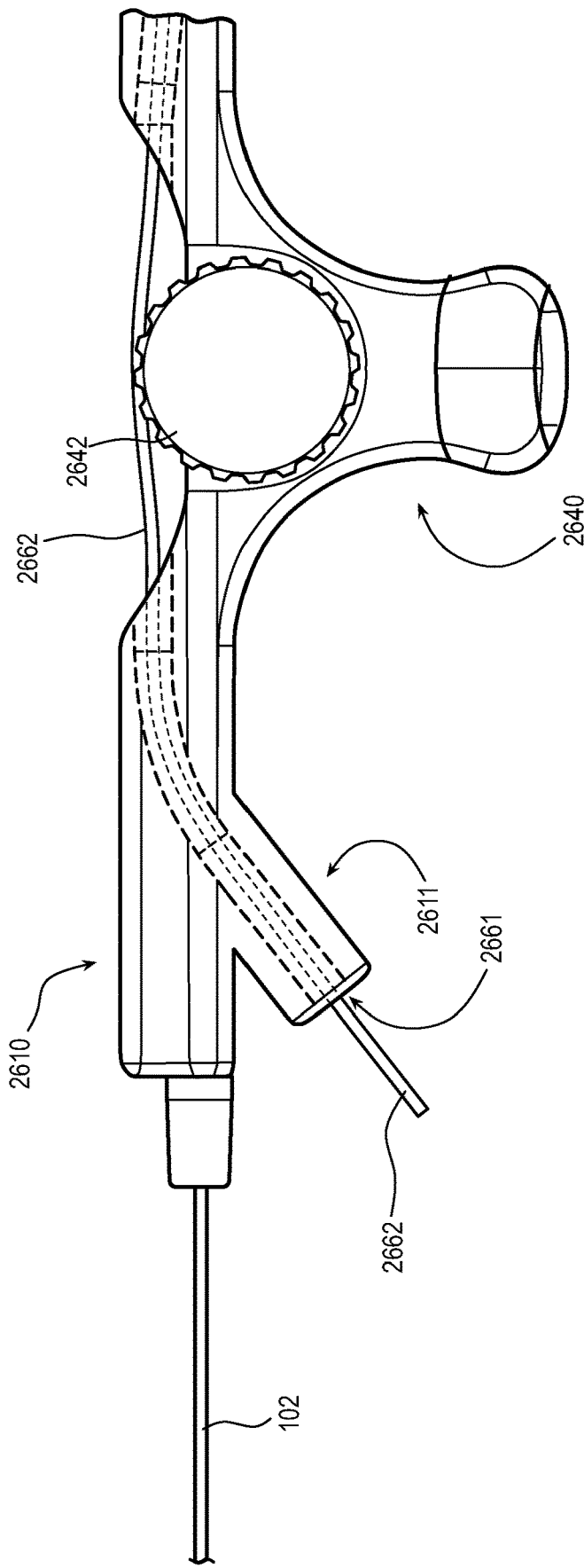

FIG. 19 provides a longitudinal cross section of the twelfth guidewire-management device in accordance with some embodiments.

Figure 20:
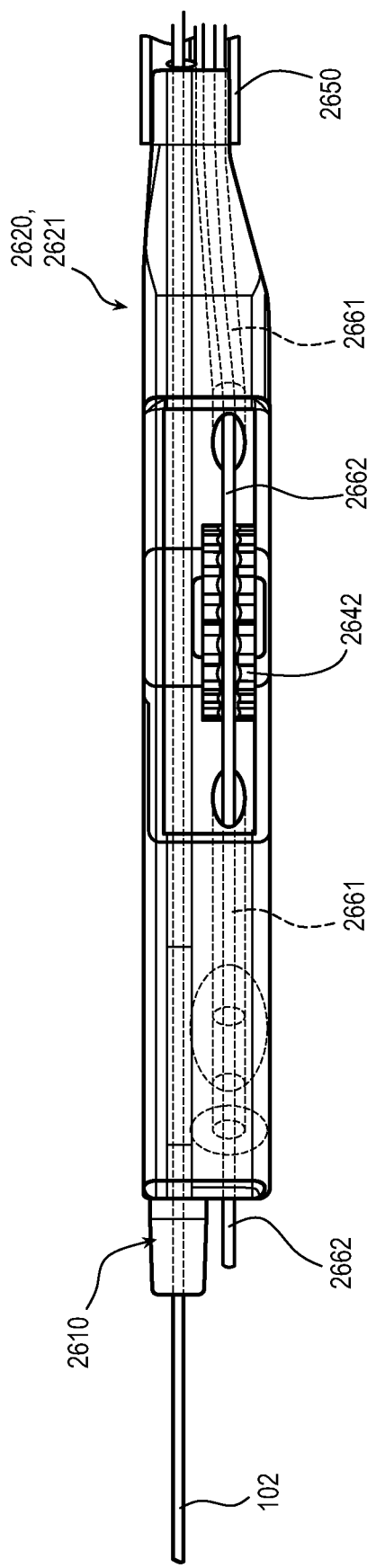

FIG. 20 provides a top view of a handle of the twelfth guidewire-management device in accordance with some embodiments.

Figure 21:
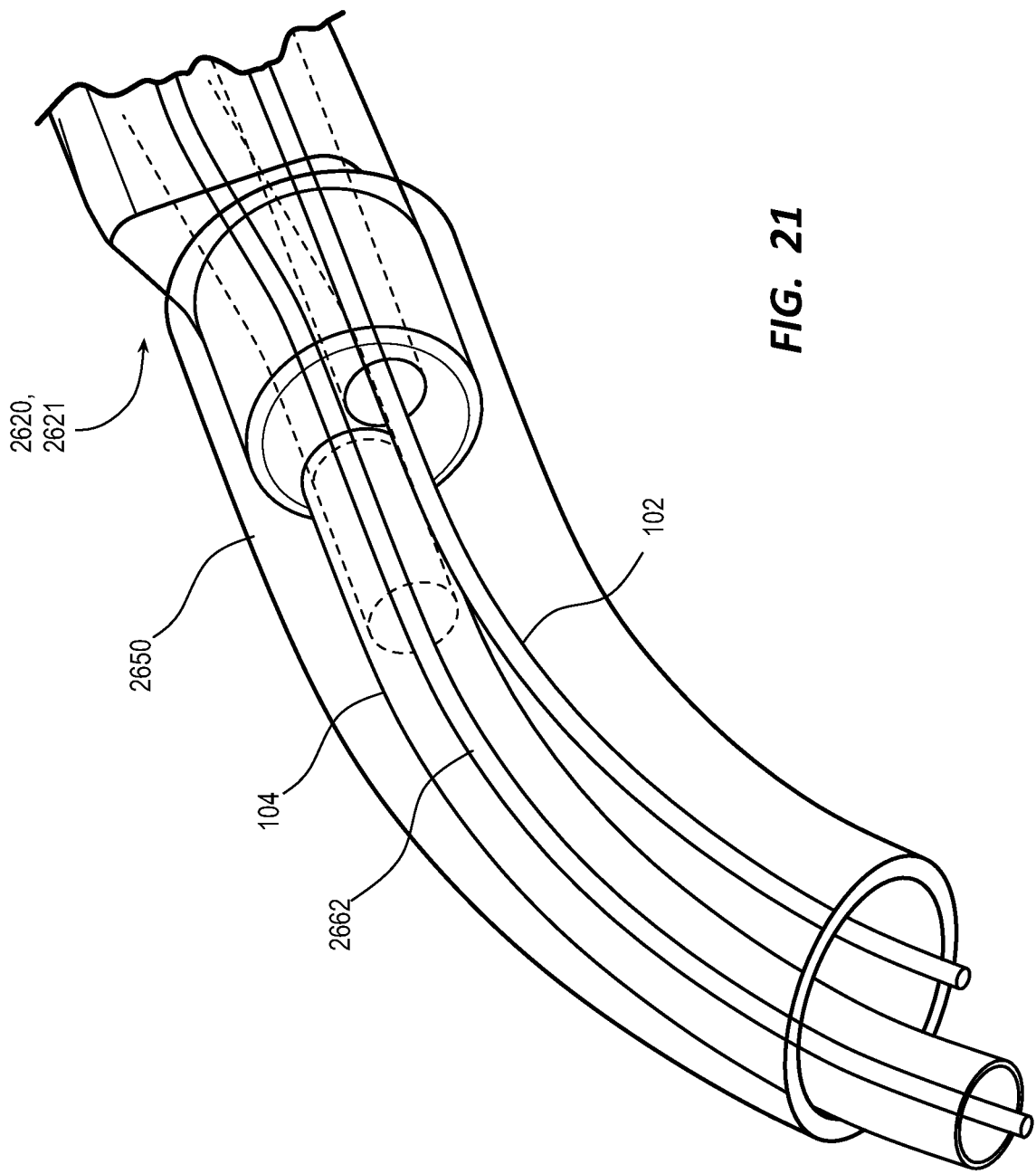

FIG. 21 provides a detailed view of a proximal portion of the handle of the twelfth guidewire-management device in accordance with some embodiments.

Figure 22:
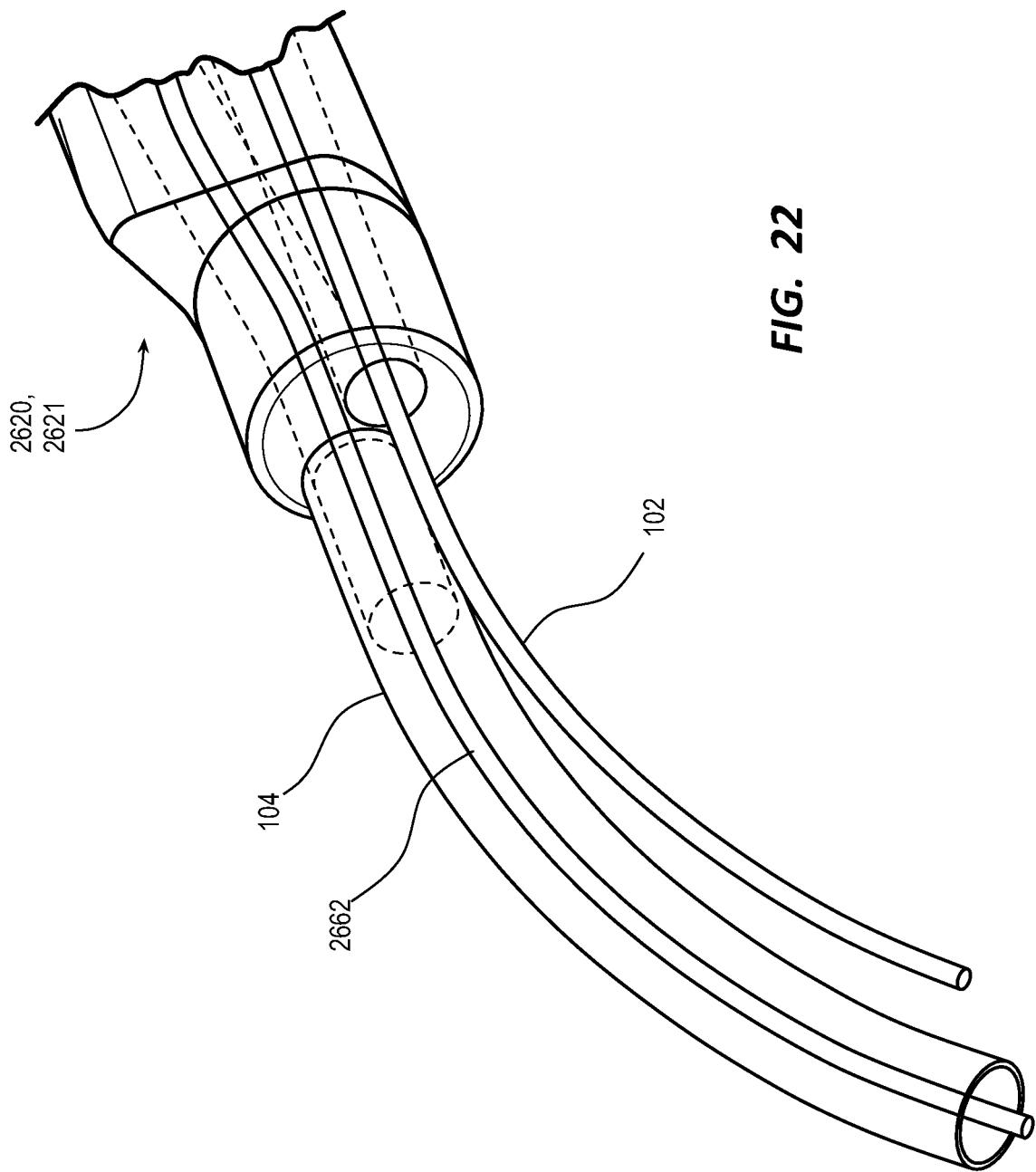

FIG. 22 provides a detailed view of the proximal portion of the handle of the twelfth guidewire-management device without a guidewire conduit in accordance with some embodiments.

Figure 23:
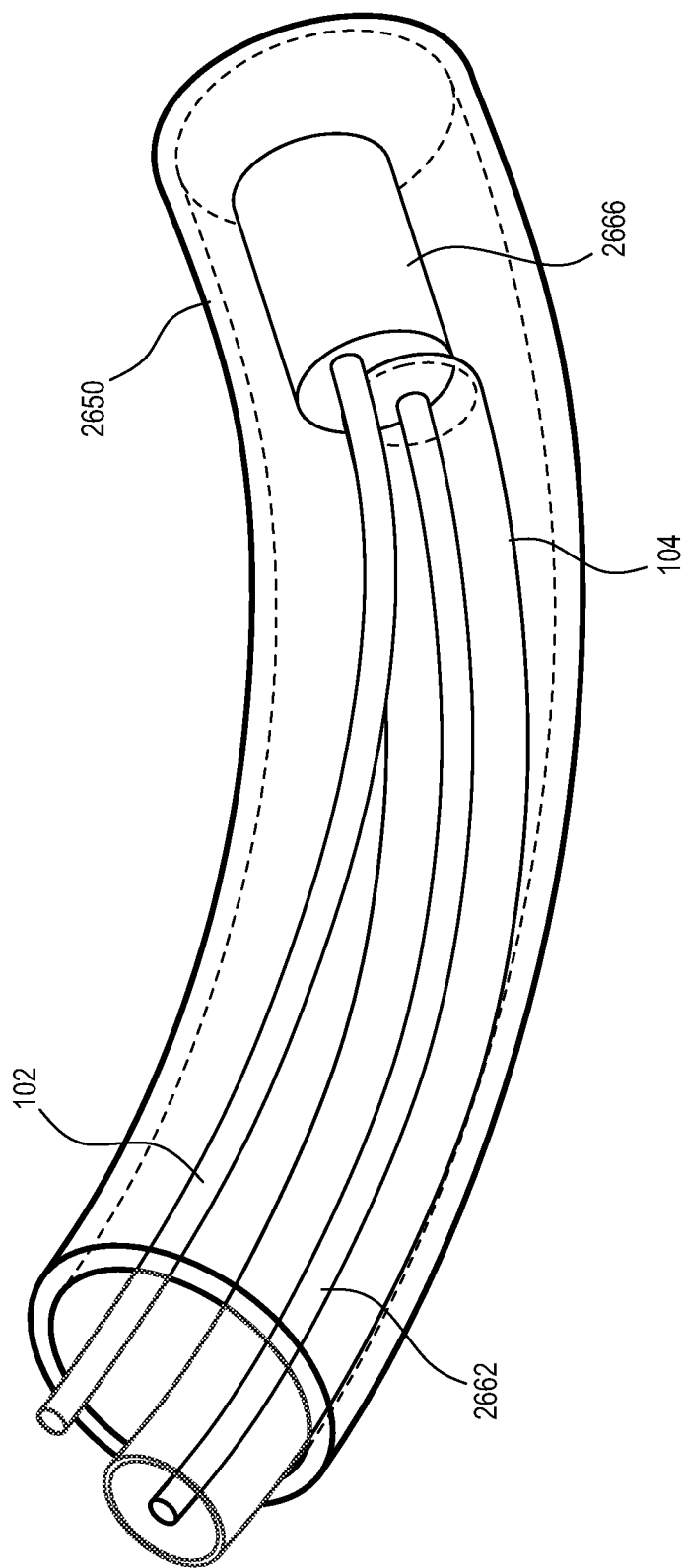

FIG. 23 provides a detailed view of the proximal portion of the guidewire conduit of the twelfth guidewire-management device in accordance with some embodiments.

Figure 24:
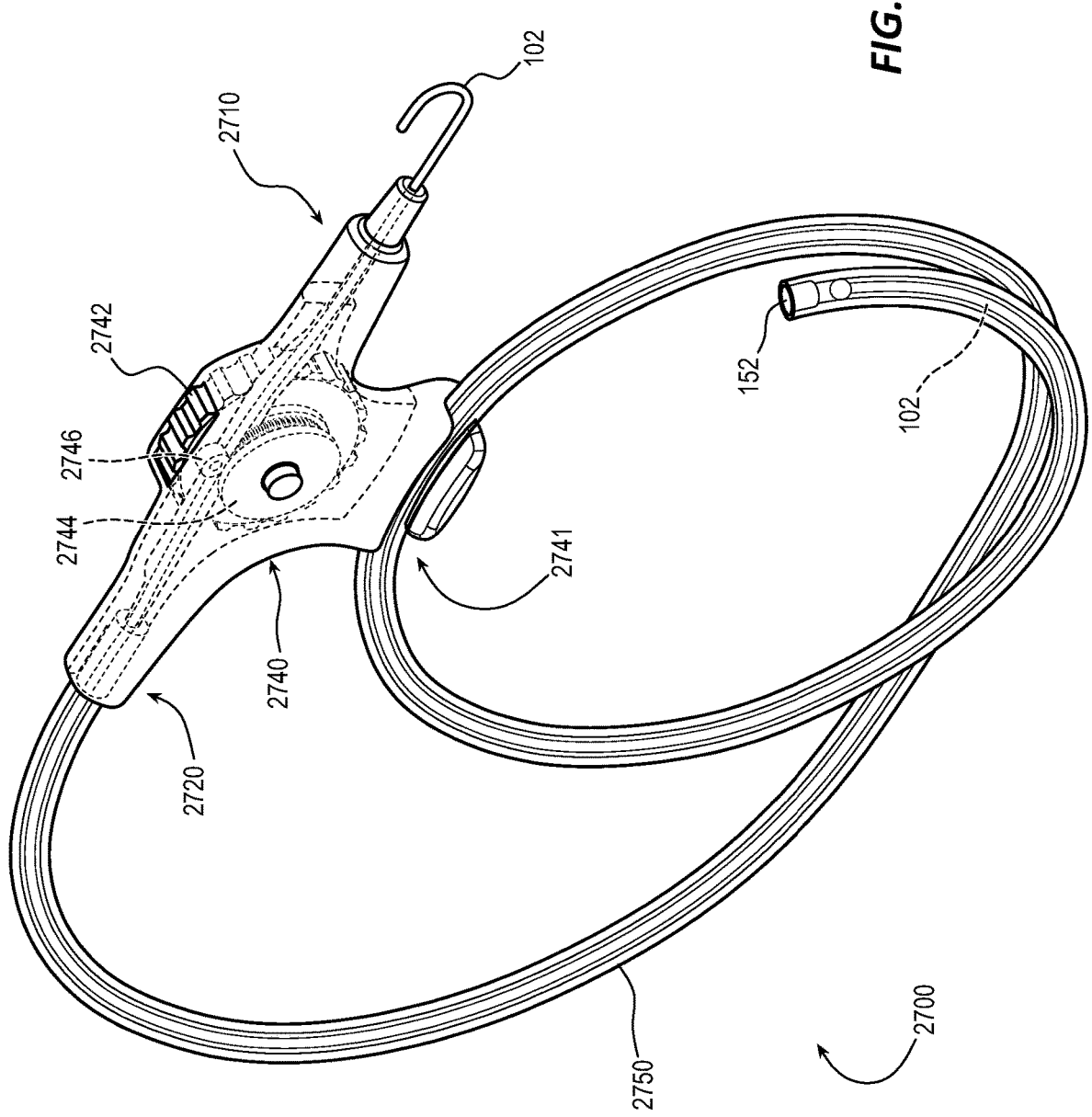

FIG. 24 provides an isometric view of a thirteenth guidewire-management device in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

With respect to "tether," a tether disclosed herein includes a tether mechanism including any tether line, tether handle, slider or other elements directly or indirectly coupled to a guidewire configured to advance or withdraw the guidewire respectively out or into a guidewire-management device.

Unless defined otherwise, all technical and scientific terms used herein have the same meaning as commonly understood by those of ordinary skill in the art.

As set forth above, there is a need for better guidewire management in medical procedures such as those requiring the Seldinger technique. Disclosed herein are guidewire-management devices and methods thereof that address the foregoing.

Guidewire-Management Devices

FIGS. 1-23 illustrate various guidewire-management devices, namely guidewire-management devices 100, 300, 600, 700, 1700, 2000, 2100, 2200, 2300, 2400, and 2600. For expository expediency, guidewire-management devices 100, 300, 600, and 700 are initially described below with an emphasis on features in common with each other and many other guidewire management devices set forth herein. Such features can be identified among the various guidewire-management devices by identical reference numbers (e.g., guidewire 102), similar reference numbers (e.g., first sleeve 110, first sleeve 610, first sleeve 710, or the like, where the leading digits of the reference numbers are different to reflect the figures or embodiments associated with the features), description, or a combination thereof. Indeed, features in common among any group of guidewire-management devices of the various guidewire-management devices 100, 300, 600, 700, 1700, 2000, 2100, 2200, 2300, 2400, and 2600 can be similarly identified. Subsequent to the initial description for the guidewire-management devices 100, 300, 600, and 700, the guidewire-management devices 100, 300, 600, 700, 1700, 2000, 2100, 2200, 2300, 2400, and 2600 are individually or collectively described below with respect to some of the unique features thereof.

As shown, the guidewire-management device 100, 300, 600, or 700 includes a guidewire 102, a first sleeve 110, 610, or 710, and a second sleeve 120, 620, or 720.

The first sleeve 110, 610, or 710 is configured with a lumen for distally feeding, or advancing, the guidewire 102 out of the guidewire-management device 100, 300, 600, or 700. The first sleeve 110, 610, or 710 has a distal portion configured as a male connector with a Luer taper for connecting the first sleeve 110, 610, or 710 to a complementary female connector such as that of a hub of a hollow needle or a catheter. The male connector is configured such that when coupled to such a complementary female connector of, for example, the foregoing catheter, the guidewire-management device 100, 300, 600, or 700 forms a single unit with the catheter, thereby enabling the single unit to be held with one hand for guidewire management (e.g., distally feeding the guidewire 102 out of the guidewire-management device 100, 300, 600, or 700. into the catheter).

The first sleeve 110, 610, or 710 has a proximal portion including a bore 112, 612 (not shown), or 712 into which the lumen of the first sleeve 110, 610, or 710 opens. The bore 112, 612, or 712 is configured to house a distal portion of a sterile barrier 104 or 304 or collect the distal portion of the sterile barrier 104 when distally feeding the guidewire 102 out of the guidewire-management device 100, 300, 600, or 700. The bore 112, 612, or 712 can include a metering mechanism such as a circumferential ridge of the bore 112, 612, or 712. Such a circumferential ridge is configured to hold back portions (e.g., pleats) of the sterile barrier 104 in the bore 112, 612, or 712 distal of the circumferential ridge subsequent to collecting the distal portion of the sterile barrier 104 in the bore 112, 612, or 712. When for proximally feeding the guidewire 102 into the guidewire-management device 100, 300, or 700 as set forth below, the sterile barrier 104 is metered out of the bore 112, 612, or 712 in portions (e.g., one pleat at a time), which facilitates proximally feeding the guidewire 102 into the guidewire-management device 100, 300, or 700 by letting out only as much of the sterile barrier 104 as immediately needed in to recover the guidewire 102.

The first sleeve 110, 610, or 710 is also configured for proximally feeding, or withdrawing, the guidewire 102 into the guidewire-management device 100, 300, 600, or 700. The first sleeve 110, 610, or 710 is configured to straighten the guidewire 102 such as a 'J'-shaped tip thereof when proximally feeding the guidewire 102 into the guidewire-management device 100, 300, 600, or 700. (See FIGS. 7 and 8 for the 'J'-shaped tip of the guidewire 102 in accordance with some embodiments.) The first sleeve 110, 610, or 710 can include a seal such as an 'O'-ring 114, 614 (not shown), or 714 configured to block fluid (e.g., blood) from entering the guidewire-management device 100, 300, 600, or 700 when proximally feeding the guidewire into the guidewire-management device 100, 300, 600, or 700. The seal, for example, the 'O'-ring 114, 614, or 714, is also configured to block fluid (e.g., air) from escaping the guidewire-management device 100, 300, 600, or 700 when proximally feeding the guidewire into the guidewire-management device 100, 300, 600, or 700, thereby minimizing or obviating risk of air embolism. The first sleeve 110, 610, or 710 can include a guidewire lock configured to lock the guidewire 102 in place when, for example, proximally feeding the guidewire 102 into the guidewire-management device 100, 300, 600, or 700 and a desired depth of the guidewire 102 in a patient has been reached. The guidewire lock can be configured to lock the guidewire 102 in place by rotating a distal-end piece of the first sleeve 110, 610, or 710 to compress the 'O'-ring 114 more tightly on the guidewire 102. Alternatively, the guidewire lock can include a ball stopper configured to move along the guidewire-management device 100, 300, 600, or 700 and tighten, so that if a clinician only deploys the guidewire 102 halfway, the clinician could adjust the guidewire lock so that the guidewire 102 would never be deployed beyond halfway.

The second sleeve 120, 620, or 720 is proximal of the first sleeve 110, 610, or 710 in the guidewire-management device 100, 300, 600, or 700 such that at least a length of the guidewire 102 extends between the first sleeve 110, 610, or 710 and the second sleeve 120, 620, or 720. At least the length of the guidewire 102 extending between the first sleeve 110, 610, or 710 and the second sleeve 120, 620, or 720 is disposed within the sterile barrier 104 or 304.

The second sleeve 120, 620, or 720 is configured with a lumen for feeding the guidewire 102 in concert with the first sleeve 110, 610, or 710 such as distally feeding the guidewire 102 out of the guidewire-management device 100, 300, 600, or 700. The second sleeve 120, 620, or 720 has a proximal portion optionally including a bore 122 into which the lumen of the second sleeve 120, 620, or 720 opens. For example, the second sleeve 120 has the proximal portion including the bore 122, whereas the second sleeve 620 or 720 has the proximal portion without such a bore. Whether or not the second sleeve 120, 620, or 720 includes such a bore, the second sleeve 120, 620, or 720 further includes a constriction 124, a recess 724, or a similar stopping means for stopping an end of the guidewire 102 having a mass such as a ball or slug end thereof from completely passing through the second sleeve 120, 620, or 720 when distally feeding the guidewire 102 out of the guidewire-management device 100, 300, 600, or 700. Since the constriction 124, the recess 724, or the similar stopping means is configured to stop the end of the guidewire 102 from completely passing through the second sleeve 120, 620, or 720, the constriction 124, the recess 724, or the similar stopping means is also configured to stop the guidewire from completely passing through the guidewire-management device 100, 300, 600, or 700 and into a patient where the guidewire 102 can be lost. That said, the mass can be configured to break off the end of the guidewire 102 when a threshold amount of tension is manually applied such as subsequent to the guidewire 102 reaching its proper depth in a patient when it is desired the guidewire be free of the guidewire-management device 100, 300, 600, or 700.

The second sleeve 120, 620, or 720 is also configured for proximally feeding the guidewire 102 into of the guidewire-management device 100, 300, 600, or 700 in concert with the first sleeve 110, 610, or 710. The second sleeve 120, 620, 720 has a distal portion including a bore 126, 626 (not shown), or 726 into which the lumen of the second sleeve 120, 620, or 720 opens. The bore 126, 626, or 726 is configured to house a proximal portion of the sterile barrier 104 or 304 or collect the proximal portion of the sterile barrier 104 or 304 when proximally feeding the guidewire 102 into of the guidewire-management device 100, 300, 600, or 700.

The guidewire 102 has a distal portion and a proximal portion.

The distal portion of the guidewire 102 can include a 'J'-shaped tip configured to straighten as the tip of the guidewire 102 enters the first sleeve 110, 610, or 710 when proximally feeding the guidewire 102 into the guidewire-management device 100, 300, 600, or 700. When distally feeding the guidewire 102 out of the guidewire-management device 100, 300, 600, or 700, the 'J'-shaped tip is configured to reform the 'J' shape upon release from its constriction (e.g., the first sleeve 110, 610, or 710). If the first sleeve 110, 610, or 710 is connected to a complementary female connector such as that of a hub of a hollow needle, the tip of the guidewire 102 does not reform the 'J' shape until the tip is distally beyond the needle such as in a blood vessel.

The proximal portion of the guidewire 102 can include a mass such as ball end of the guidewire 102 configured to stop the guidewire 102 from completely passing through the second sleeve 120, 620, or 720 on account of the constriction 124, the recess 724, or the similar stopping means when distally feeding the guidewire 102 out the guidewire-management device 100, 300, 600, or 700.

The sterile barrier 104 or 304 is configured to maintain sterility of the guidewire 102 while the guidewire 102 is disposed therein. Importantly, the guidewire never needs to be touched by a clinician during a procedure, thereby preserving the sterility of the guidewire 102 as well as ensuring the clinician remains free from contact with bodily fluids.

The sterile barrier 104 is a pleated bag. The sterile barrier 104, or the bag 104, is configured to unpleat as it is drawn from the second sleeve 120, of the guidewire-management device 100 or pass through the second sleeve 620, or 720 of the guidewire-management device 600 or 700 while distally feeding the guidewire 102 out of the guidewire-management device 100, 600, or 700. The bag 104 is also configured to pleat as it is inserted into the first sleeve 110, 610, or 710 while distally feeding the guidewire 102 out of the guidewire-management device 100, 600, or 700. Likewise, the bag 104 is configured to unpleat as it is drawn from the first sleeve 110, 610, or 710 while proximally feeding the guidewire 102 into the guidewire-management device 100, 600, or 700. The bag 104 is also configured to pleat as it is inserted into the second sleeve 120, 620, or 720 of the guidewire-management device 100 or pass through the second sleeve 620 or 720 of the guidewire-management device 600 or 700 while proximally feeding the guidewire 102 into the guidewire-management device 100, 600, or 700.

Advantageously, in guidewire-management devices such as the guidewire-management devices 600 and 700, a combination of a length of the bag 104, a sealed (e.g., heat crimped) proximal end of the bag 104, and an attached distal end of the bag 104 is configured to provide a stop for the end (e.g., ball end) of the guidewire 102 when proximally feeding the guidewire 102 into the guidewire-management device 600 or 700. That is, the proximal end of the bag 104, itself, provides a stop when proximally feeding the guidewire 102 into the guidewire-management device 600 or 700 and the bag 104 reaches its maximum length from where it is attached to the guidewire-management device 600 or 700. Stopping the end of the guidewire 102 from passing through the proximal end of the bag 104 prevents the tip of the guidewire 102 from completely passing through the first sleeve 110 and reforming the 'J'-shaped tip when proximally feeding the guidewire 102 into the guidewire-management device 600 or 700.

A method for distally feeding, or advancing, the guidewire 102 out of the guidewire-management device 100, 600, or 700 is set forth below. A method for proximally feeding, or withdrawing, the guidewire 102 into the guidewire-management device 100, 600, or 700 is also set forth below.

The sterile barrier 304 is a bellowed boot. The sterile barrier 304, or the boot 304, is configured to iteratively stretch from an equilibrium state and relax back into the equilibrium state while distally feeding the guidewire 102 out of the guidewire-management device 300. Likewise, the boot 304 is configured to iteratively stretch from an equilibrium state and relax back into the equilibrium state while proximally feeding the guidewire 102 into the guidewire-management device 300.

A method for distally feeding, or advancing, the guidewire 102 out of the guidewire-management device 300 is set forth below. A method for proximally feeding, or withdrawing, the guidewire 102 into the guidewire-management device 300 is also set forth below.

While not shown for any guidewire-management device of the guidewire-management devices 100, 300, 600, and 700, the sterile barrier 104 or 304 can alternatively be a splittable casing 1204 (see FIG. 12) over an entirety of the guidewire 102 or at least most of the guidewire 102, for example, excepting that within or distal to the first sleeve 110, 610, or 710. The splittable casing 1204 is configured to split off the guidewire 102 while distally feeding the guidewire 102 out of a guidewire-management device. (See, for example, the guidewire-management devices 1700, 2000, 2100, 2200, 2300, and 2400.) Some of the foregoing guidewire-management devices are configured to insert the guidewire 102 into the splittable casing 1204 while proximally feeding the guidewire 102 into the guidewire-management devices. The splittable casing 1204 can include graduated markings thereon configured to indicate a length of the guidewire 102 from the tip thereof.

Adverting to FIGS. 1-4 to describe some of the unique features of least the guidewire-management devices 100 and 300, the guidewire-management devices 100 and 300 include the guidewire 102, a frame 140 including a pair of tubular rails 142, a guidewire conduit 150 threaded through the pair of tubular rails 142, the first sleeve 110 mounted on struts between each rail of the pair of tubular rails 142, and the second sleeve 120 mounted on struts between each rail of the pair of tubular rails 142 proximal of the first sleeve 110. At least a portion of the guidewire 102 is disposed within the guidewire conduit 150.

The guidewire conduit 150 can be opaque or translucent depending upon a chosen polymeric material. When the guidewire conduit 150 is translucent, the guidewire conduit 150 is configured for viewing the guidewire 102 while distally feeding the guidewire 102 out of the guidewire-management device 100 or 300 or proximally feeding the guidewire 102 into the guidewire-management device 100 or 300.

FIG. 5 illustrates the ball end of the guidewire 102 distal to a plug 152 in the guidewire conduit 150 in accordance with some embodiments.

The guidewire conduit 150 has a proximal portion including the plug 152 configured to stop the ball end of the guidewire 102 (or any similar mass at the end of the guidewire 102) from passing through what would otherwise be an opening in a proximal end of the guidewire conduit 150. Alternatively, the plug 152 is simply a crimped portion of the guidewire conduit 150 with the same effect. Stopping the ball end of the guidewire 102 from passing through such an opening in the guidewire conduit 150 prevents the tip of the guidewire 102 from completely passing through the first sleeve 110 and reforming the 'J'-shaped tip when proximally feeding the guidewire 102 into the guidewire-management device 100 or 300.

Adverting to FIGS. 6-8 to describe some of the unique features of at least the guidewire-management devices 600 and 700, the guidewire-management device 600 or 700 includes a handle 640 or 740, the guidewire 102, the first sleeve 610 or 710 formed in a distal portion of the handle 640 or 740, the second sleeve 620 or 720 formed in a proximal portion of the handle 640 or 740, and a thumb wheel 642 or 742 disposed under the guidewire 102 between the first sleeve 610 or 710 and the second sleeve 620 or 720.

The handle 640 or 740 is ambidextrous in that it is configured to be held in either a right or left hand of a clinician. In addition, the handle 640 or 740 is configured to be held in at least two different modes. The first mode, in which the clinician holds the handle 640 or 740 like a person might hold the handle of a hammer, is a general mode for handling the guidewire-management device 600 or 700. The second mode, in which the clinician repositions his or her thumb over the thumb wheel 642 or 742, is an operational mode for advancing the guidewire 102 out of the guidewire-management device 600 or 700 or withdrawing the guidewire 102 into the guidewire-management device 600 or 700. Notwithstanding the foregoing, some clinicians might find it comfortable to hold the handle 640 or 740 like a person might hold the barrel of a flashlight, thereby accessing both the first and second modes with less hand movement.

The handle 640 includes a channel 641 configured to hold a conduit therein. The conduit can be a guidewire conduit, a guidewire-casing conduit, or the like. Advantageously, such a channel can hold a conduit in a coiled configuration, thereby packing an otherwise elongate conduit into a compact space. While only the handle 640 is shown with any channels, the handle 740 can include a channel configured to hold a conduit. In addition, the handle 640 need not include the channel 641.

The thumb wheel 642 or 742 can be rotatably mounted on an axle fixedly coupled to each side of the handle 640 or 740 such that the thumb wheel 642 or 742 rotates relative to both the axle and the handle 640 or 740. Alternatively, the thumb wheel 642 or 742 can include the axle (e.g., as a unitary piece) or be fixedly mounted on the axle, which, in turn, is rotatably coupled to each side of the handle 640 or 740 such that a combination of the thumb wheel 642 or 742 and the axle rotates with respect to the handle 640 or 740. The thumb wheel 642 or 742 is configured to assist in distally feeding the guidewire 102 out of the guidewire-management device 600 or 700 by way of the first sleeve 610 or 710. The thumb wheel 642 or 742 is also configured to assist in proximally feeding the guidewire 102 into the guidewire-management device 600 or 700 by way of the first sleeve 610 or 710.

A method for distally feeding, or advancing, the guidewire 102 out of the guidewire-management device 600 or 700 is set forth below. A method for proximally feeding, or withdrawing, the guidewire 102 into the guidewire-management device 600 or 700 is also set forth below.

Adverting to FIGS. 9-11 to describe some of the unique features of at least the guidewire-management device 1700, the guidewire-management device 1700 includes a handle 1740, the guidewire 102, a first sleeve 1710 formed in a distal portion of the handle 1740, a second sleeve 1720 formed in a proximal portion of the handle 1740, a guidewire-gripping wheel 1742 disposed under the guidewire 102 between the first sleeve 1710 and the second sleeve 1720 configured to grip the guidewire when the guidewire-gripping wheel 1742 is turned, and a knob 1744 coupled to the guidewire-gripping wheel 1742. The guidewire 102 extends between the first sleeve 1710 and the second sleeve 1720 but is disposed within a capsule 1746 functioning as a sterile barrier to maintain sterility of the guidewire 102 between the first sleeve 1710 and the second sleeve 1720. In addition to the capsule 1746, the guidewire-management device 1700 includes a guidewire conduit 1750 coupled to the second sleeve 1720 configured to maintain sterility of the guidewire 102 outside of the first sleeve 1710, the capsule 1746, and the second sleeve 1720. Because both the capsule 1746 and the guidewire conduit 1750 are configured to maintain sterility of the guidewire, a sterile barrier such as the bag 104 or the splittable casing 1204 is not needed for the guidewire-management device 1700.

Notwithstanding possible differences in one or more design elements, the handle 1740 is similar to the handle 640 set forth above. As such, the description set forth above for the handle 640 should be understood to extend to the handle 1740 as if the handle 1740 was included in the description of the handle 640. This includes the description for the channel 641 as the handle 1740 analogously includes a channel 1741.

Notwithstanding possible differences in one or more design elements, the first sleeve 1710 is similar to the first sleeve 110, 610, or 710 set forth above. As such, the description set forth above for the first sleeves 110, 610, and 710 should be understood to extend to the first sleeve 1710 as if the first sleeve 1710 was included in the description of the first sleeves 110, 610, and 710.

Notwithstanding possible differences in one or more design elements, the second sleeve 1720 is similar to the second sleeve 120, 620, or 720 set forth above. As such, the description set forth above for the second sleeves 120, 620, and 720 should be understood to extend to the second sleeve 1720 as if the second sleeve 1720 was included in the description of the second sleeves 120, 620, and 720.

A combination of the guidewire-gripping wheel 1742 and the knob 1744 is configured for distally feeding the guidewire 102 out of the guidewire-management device 1700 or proximally feeding the guidewire 102 into the guidewire-management device 1700. Indeed, the guidewire-gripping wheel 1742 includes an axle (e.g., as a unitary piece) fixedly coupled to the knob 1744 such that the guidewire-gripping wheel 1742 rotates with the knob 1744 when the knob 1744 is rotated relative to the handle 1740. Alternatively, the knob 1744 includes an axle (e.g., as a unitary piece) and the guidewire-gripping wheel 1742 is fixedly coupled to the axle of the knob 1744 such that the guidewire-gripping wheel 1742 rotates with the knob 1744 when the knob 1744 is rotated relative to the handle 1740. Further alternatively, the guidewire-gripping wheel 1742 and the knob 1744 are independently fixedly coupled to an axle such that the guidewire-gripping wheel 1742 rotates with the knob 1744 when the knob 1744 is rotated relative to the handle 1740. In this way, the combination of the guidewire-gripping wheel 1742 and the knob 1744 is configured to assist in distally feeding the guidewire 102 out of the guidewire-management device 1700 by way of the first sleeve 1710 such as when the knob 1744 is rotated clockwise. The combination of the guidewire-gripping wheel 1742 and the knob 1744 can be configured to slip when a threshold amount of pressure is experienced while distally feeding the guidewire 102 out of the guidewire-management device 1700. The combination of the guidewire-gripping wheel 1742 and the knob 1744 is also configured to assist in proximally feeding the guidewire 102 into the guidewire-management device 1700 by way of the first sleeve 1710 such as when the knob 1744 is rotated counterclockwise. The guidewire-gripping wheel 1742 includes teeth configured to gently press the guidewire 102 against the capsule 1746 and grip the guidewire 102 using the resulting friction for distally feeding the guidewire 102 out of the guidewire-management device 1700 or proximally feeding the guidewire 102 into the guidewire-management device 1700.

The capsule 1746 extends between the first sleeve 1710 and the second sleeve 1720 over the guidewire 102, thereby maintaining sterility of the guidewire 102 between the first sleeve 1710 and the second sleeve 1720. The capsule 1746 is configured to provide a backing against which the guidewire-gripping wheel 1742 gently presses the guidewire 102 in order to grip the guidewire 102 for distally feeding the guidewire 102 out of the guidewire-management device 1700 or proximally feeding the guidewire 102 into the guidewire-management device 1700. The capsule 1746 can be translucent for viewing the guidewire 102 while it is either distally fed out of the guidewire-management device 1700 or proximally fed into the guidewire-management device 1700. That said, the capsule 1746 can be opaque as it is also possible to view the guidewire 102 in the guidewire conduit 1750 while it is either distally fed out of the guidewire-management device 1700 or proximally fed into the guidewire-management device 1700 if the guidewire conduit 1750 is translucent as set forth below.

The guidewire conduit 1750 is configured to distally feed the guidewire 102 into the guidewire-management device 1700 by way of the second sleeve 1720 while distally feeding the guidewire 102 out of the guidewire-management device 1700, as well as collect the guidewire 102 back in the guidewire conduit 1750 by way of the second sleeve 1720 while proximally feeding the guidewire 102 into the guidewire-management device 1700. The guidewire conduit 1750 can be opaque or translucent depending upon a chosen polymeric material. When the guidewire conduit 1750 is translucent, the guidewire conduit 1750 is configured for viewing the guidewire 102 while distally feeding the guidewire 102 into the guidewire-management device 1700 or collecting the guidewire 102 back in the guidewire conduit 1750 while proximally feeding the guidewire 102 into the guidewire-management device 1700.

The guidewire-management device 1700 can further include one or more guidewire-conduit clips 1758 configured to hold different portions of the guidewire conduit 1750 therein. Advantageously, the guidewire-conduit clips 1758 can hold the guidewire conduit 1750 in a coiled configuration, thereby packing the otherwise elongate guidewire conduit 1750 into a compact space.

Adverting to FIGS. 12 and 13 to describe some of the unique features of at least the guidewire-management device 2000 or 2100, the guidewire-management device 2000 or 2100 includes a handle 2040 or 2140, the guidewire 102, a first sleeve 2010 or 2110 formed in a distal portion of the handle 2040 or 2140, a second sleeve 2020 or 2120 formed in a proximal portion of the handle 2040 or 2140, and a gapped guidewire conduit 2050 or 2150 coupled to the second sleeve 2020 or 2120.

Notwithstanding certain differences in one or more design elements such as the lack of a thumb wheel (e.g., the thumb wheel 642), the handle 2040 or 2140 is similar to the handle 640 set forth above. As such, the description set forth above for the handle 640 should be understood to extend to the handle 2040 or 2140 as if the handle 2040 or 2140 was included in the description of the handle 640. This includes the description for the channel 641 as the handle 2040 or 2140 analogously includes a channel (not shown). As alluded to, however, the handle 2040 or 2140 does not include a thumb wheel such as the thumb wheel 642 of the handle 640, so the description set forth above for the foregoing does not extend to the handle 2040 or 2140. Instead, the handle 2040 or 2140 includes a ridge 2042 or 2142 between the first sleeve 2010 or 2110 and the second sleeve 2020 or 2120. The ridge 2042 or 2142 can be arcuate and textured (e.g., transversely grooved) as shown, which ridge 2042 or 2142 is configured to provide a tactile sense of place should a clinician choose to gently press the guidewire 102 into the ridge 2042 or 2142 with his or her thumb and use the resulting pressure to distally feed the guidewire 102 out of the guidewire-management device 2000 or 2100 or proximally feed the guidewire 102 into the guidewire-management device 2000 or 2100.

Notwithstanding possible differences in one or more design elements, the first sleeve 2010 or 2110 is similar to the first sleeve 110, 610, or 710 set forth above. As such, the description set forth above for the first sleeves 110, 610, and 710 should be understood to extend to the first sleeves 2010 and 2110 as if the first sleeves 2010 and 2110 were included in the description of the first sleeves 110, 610, and 710.

Notwithstanding possible differences in one or more design elements, the second sleeve 2020 or 2120 is similar to the second sleeve 120, 620, or 720 set forth above. As such, the description set forth above for the second sleeves 120, 620, and 720 should be understood to extend to the second sleeves 2020 and 2120 as if the second sleeve 2020 and 2120 were included in the description of the second sleeves 120, 620, and 720.

The gapped guidewire conduit 2050 or 2150 includes a gap 2056 or 2156 in the gapped guidewire conduit 2050 or 2150 proximal of the second sleeve 2020 or 2120. The gap 2056 or 2156 is configured to expose the guidewire 102 in the gapped guidewire conduit 2050 or 2150 such that the guidewire 102 can be grasped (e.g., between a thumb and index finger) and distally fed into the guidewire-management device 2000 or 2100 by way of the second sleeve 2020 or 2120. When the guidewire 102 is distally fed into the guidewire-management device 2000 or 2100 by way of the second sleeve 2020 or 2120, the guidewire 102 is also distally fed out of the guidewire-management device 2000 of 2100 by way of the first sleeve 2010 or 2110. The gap 2056 or 2156 is also configured to expose the guidewire 102 in the gapped guidewire conduit 2050 or 2150 such that the guidewire 102 can be grasped (e.g., between a thumb and index finger) and proximally fed into the gapped guidewire conduit 2050 or 2150 by way of the second sleeve 2020 or 2120. When the guidewire 102 is proximally fed into the gapped guidewire conduit 2050 or 2150 by way of the second sleeve 2020 or 2120, the guidewire 102 is also proximally fed into of the guidewire-management device 2000 of 2100 by way of the first sleeve 2010 or 2110. Proximally or distally feeding the guidewire 102 by way of the guidewire 102 exposed by the gap 2056 or 2156 is useful for feeding the guidewire 102 in large or small bits for rough or fine adjustments of the guidewire 102, whereas a clinician might find proximally or distally feeding the guidewire 102 by way of the guidewire 102 over the ridge 2042 or 2142 as set forth above more suitable for proximally or distally feeding the guidewire 102 in small bits for fine adjustments of the guidewire 102.

The guidewire-management device 2000 or 2100 can further include one or more guidewire-conduit clips, for example, the guidewire-conduit clips 2058, configured to hold different portions of the gapped guidewire conduit 2050 therein. While the guidewire-conduit clips advantageously hold the gapped guidewire conduit 2050 or 2150 in a coiled configuration as set forth above with respect to guidewire-management device 1700, the guidewire-conduit clips further advantageously provide structural integrity to the gapped guidewire conduit 2050 or 2150 when placed on both sides of the gap 2056 or 2156.

Due to the configuration of the guidewire-management device 2000 or 2100 requiring direct handling of the guidewire 102, an entirety of the guidewire 102 is disposed within a sterile barrier such as the bag 104 or the splittable casing 1204 excepting, for example, any portion of the guidewire 102 within or distal to the first sleeve 2010 or 2110. If the sterile barrier is the bag 104, the first sleeve 2010 or 2110 includes a bore such as the bore 112, 612, or 712 of the guidewire-management device 100, 600, or 700 in a proximal portion of the first sleeve 2010 or 2110 such that the bag 104 can pleat as the bag 104 is inserted into the first sleeve 2010 while distally feeding the guidewire 102 out of the guidewire-management device 2000 or 2100. If the sterile barrier is the splittable casing 1204, the splittable casing 1204 is configured to split off the guidewire 102 while distally feeding the guidewire out of the guidewire-management device 2000 or 2100.

The guidewire-management device 2000 or 2100 can be configured with or without a first split sleeve for discharging the splittable casing 1204 that splits off the guidewire 102 while distally feeding the guidewire 102 out of the guidewire-management device 2000 or 2100. For example, the guidewire-management device 2000 is shown without such a first split sleeve. In such embodiments, the splittable casing 1204 that splits off the guidewire 102 while distally feeding the guidewire 102 out of the guidewire-management device 2000 splits off the guidewire 102 between the first sleeve 2010 and the second sleeve 2020 and discharges off to a side of the handle 2040. However, the guidewire-management device 2100 is shown with a first split sleeve 2111. In such embodiments, the first split sleeve 2111 is configured to discharge the splittable casing 1204 while distally feeding the guidewire 102 out of the guidewire-management device 2100. Whether or not the guidewire-management device 2000 or 2100 includes a split sleeve, a clinician might find it useful to distally feed the guidewire 102 by pulling on the splittable casing 1204 that splits off the guidewire 102 as if a tether. Indeed, the clinician might find distally feeding the guidewire 102 in such a way more suitable for distally feeding the guidewire 102 in large bits for rough adjustments of the guidewire 102.

Adverting to FIGS. 14 and 15 to describe some of the unique features of at least the guidewire-management device 2200 or 2300, the guidewire-management device 2200 or 2300 includes a handle 2240 or 2340, the guidewire 102, a first sleeve 2210 or 2310 formed in a distal portion of the handle 2240 or 2340, a second sleeve 2220 or 2320 formed in a proximal portion of the handle 2240 or 2340, a guidewire conduit 2250 or 2350 coupled to the second sleeve 2220 or 2320, and a tether such as the tether 2360 coupled to a proximal portion of the guidewire 102 and disposed in the guidewire conduit 2250 or 2350 along with the guidewire.

Notwithstanding possible differences in one or more design elements such as a tether channel 2361 extending through at least a portion of the handle 2340 including a tether line of the guidewire-management device 2300, the handle 2240 or 2340 is similar to the handle 640 set forth above. As such, the description set forth above for the handle 640 should be understood to extend to the handle 2240 or 2340 as if the handle 2240 or 2340 was included in the description of the handle 640. This includes the description for the channel 641 as the handle 2240 or 2340 analogously includes a channel (not shown).

Notwithstanding possible differences in one or more design elements, the first sleeve 2210 or 2310 is similar to the first sleeve 110, 610, or 710 set forth above. As such, the description set forth above for the first sleeves 110, 610, and 710 should be understood to extend to the first sleeve 2210 or 2310 as if the first sleeve 2210 or 2310 was included in the description of the first sleeves 110, 610, and 710.

Notwithstanding possible differences in one or more design elements, the second sleeve 2220 or 2320 is similar to the second sleeve 120, 620, or 720 set forth above. As such, the description set forth above for the second sleeves 120, 620, and 720 should be understood to extend to the second sleeve 2220 or 2320 as if the second sleeve 2220 or 2320 was included in the description of the second sleeves 120, 620, and 720.

The guidewire-management device 2200 or 2300 can include a membrane 2206 (not shown) or 2306 or a capsule 2246 (not shown) or 2346 extending between the first sleeve 2210 or 2310 and the second sleeve 2220 or 2320 over the guidewire 102, thereby maintaining sterility of the guidewire 102 between the first sleeve 2210 or 2310 and the second sleeve 2220 or 2320. If the guidewire-management device 2200 or 2300 includes the membrane 2206 or 2306, the guidewire-management device 2200 or 2300 can further include a thumb wheel such as the thumb wheel 1242 set forth above with respect to the guidewire-management device 1200 or a ridge such as the ridge 2042 or 2142 set forth above with respect to the guidewire-management device 2000 or 2100. While the tether is configured for distally feeding the guidewire 102 out of the guidewire-management device 2200 or 2300 as set forth below, the thumb wheel can be configured for at least proximally feeding the guidewire 102 into the guidewire-management device 2200 or 2300. Likewise, the ridge can be configured for at least proximally feeding the guidewire 102 into the guidewire-management device 2200 or 2300 as set forth above with respect to at least the guidewire-management device 2000 or 2100. If the guidewire-management device 2200 or 2300 includes the capsule 2246 or 2346, the guidewire-management device 2200 or 2300 can further include a knob coupled to a guidewire-gripping wheel. While the tether is configured for distally feeding the guidewire out of the guidewire-management device 2200 or 2300 as set forth below, the knob and guidewire-gripping wheel can be configured for at least proximally feeding the guidewire 102 into the guidewire-management device 2200 or 2300.

The guidewire conduit 2250 or 2350 is configured to maintain sterility of the guidewire 102 outside of the first sleeve 2210 or 2310, the membrane 2206 (not shown) or 2306 or the capsule 2246 (not shown) or 2346, and the second sleeve 2220 or 2320. The guidewire conduit 2250 or 2350 is configured to distally feed the guidewire 102 into the guidewire-management device 2200 or 2300 by way of the second sleeve 2220 or 2320 while distally feeding the guidewire 102 out of the guidewire-management device 2200 or 2300, as well as collect the guidewire 102 back in the guidewire conduit 2250 or 2350 by way of the second sleeve 2220 or 2320 while proximally feeding the guidewire 102 into the guidewire-management device 1200 or 2300. The guidewire conduit 2250 or 2350 can be opaque or translucent depending upon a chosen polymeric material. When the guidewire conduit 2250 or 2350 is translucent, the guidewire conduit 2250 or 2350 is configured for viewing the guidewire 102 while distally feeding the guidewire 102 into the guidewire-management device 2200 or 2300 or collecting the guidewire 102 back in the guidewire conduit 2250 or 2350 while proximally feeding the guidewire 102 into the guidewire-management device 2200 or 2300. As shown in FIG. 14, the guidewire conduit 2250 of the guidewire-management device 2300 can include an opening proximal of the second sleeve 2220 through which a tether line can be pulled.

The guidewire-management device 2200 or 2300 can further include one or more guidewire-conduit clips 2258 or 2358 configured to hold different portions of the guidewire conduit 2250 or 2350 therein. The guidewire-conduit clips 2258 or 2358 advantageously hold the guidewire conduit 2250 or 2350 in a coiled configuration.

With respect to the guidewire-management device 2200, the guidewire 102 is disposed in the splittable casing 1204 while in the guidewire conduit 2350, and the tether line is the splittable casing 1204 split off the guidewire 102 that extends through the opening of the guidewire conduit 2250 proximal of the second sleeve 2220. The tether is configured to distally feed the guidewire 102 out of the guidewire-management device 2200 by way of the first sleeve 2210 when the tether line is pulled out of the opening of the guidewire conduit 2250 and away from the guidewire-management device 2200. In concert with pulling the tether line out of the opening of the of the guidewire conduit 2250, additional splittable casing 1204 splits off the guidewire 102 before the guidewire 102 exits the first sleeve 2210. Proximally feeding the guidewire 102 into the guidewire-management device 2200 by way of the first sleeve 2210 can be effectuated by the thumb wheel, the ridge, or the knob and guidewire-gripping wheel depending upon which feature the guidewire-management device 2200 includes, if any. Without any one of the thumb wheel, the ridge, or the knob and guidewire-gripping wheel, the guidewire-management device 2200 is configured for removing the guidewire 102 from a patient by hand.

With respect to the guidewire-management device 2300, the guidewire 102 is either bare or disposed in the splittable casing 1204 while in the guidewire conduit 2350. When the guidewire 102 is bare, a proximal portion of a tether line 2362 (e.g., a cord, a wire, etc.) is coupled to a proximal portion of the guidewire 102 in the guidewire conduit 2350. When the guidewire 102 is disposed in the splittable casing 1204, the tether line 2362 is the splittable casing 1204 split off the guidewire 102 akin to that of the guidewire-management device 2200. In any case, a distal portion of the tether line 2362 can extend from the guidewire conduit 2350, through the tether channel 2361 extending through the handle 2340, and out an opening in the handle 2340. The distal portion of the tether line 2362 such as a distal end thereof can be coupled to a tether handle 2364 as shown. The tether 2360 is configured to distally feed the guidewire 102 out of the guidewire-management device 2300 by way of the first sleeve 2310 when the tether line 2362 is pulled out of the opening in the handle 2340 and away from the guidewire-management device 2300. As an alternative to the tether handle 2364, the distal portion of the tether line 2362 is coupled to a slider disposed in a slot of the handle 2340, thereby providing an alternative user interface for at least distally feeding the guidewire 102 out of the guidewire-management device 2300. The slider can include a bifurcated clip slidably disposed around the tether line 2362 such that when the slider is pressed into a narrowed slider channel of the handle 2340 inboard of the slot and simultaneously moved distally, the slider grips the tether line 2362 and distally feeds the guidewire 102 out of the guidewire-management device 2300 by way of the first sleeve 2310. In concert with pulling the tether line 2362 out of the opening in the handle 2340 or advancing the slider when the guidewire 102 is disposed in the splittable casing 1204, additional splittable casing 1204 splits off the guidewire 102 before the guidewire 102 exits the first sleeve 2310. Proximally feeding the guidewire 102 into the guidewire-management device 2200 by way of the first sleeve 2310 can be effectuated by pushing the tether line 2362 of the tether 2360 into the tether channel 2361 if the tether line 2362 is sufficiently stiff (e.g., a wire) or pressing the slider into the narrowed slider channel of the handle 2340 and simultaneously moving the slider proximally. Alternatively, proximally feeding the guidewire 102 into the guidewire-management device 2200 by way of the first sleeve 2310 can be effectuated by the thumb wheel, the ridge, or the knob and guidewire-gripping wheel depending upon which feature the guidewire-management device 2300 includes, if any. Without a sufficiently stiff tether line 2362 or any one of the slider, thumb wheel, the ridge, or the knob and guidewire-gripping wheel, the guidewire-management device 2300 is configured for removing the guidewire 102 from a patient by hand.

Adverting to FIGS. 16 and 17 to describe some of the unique features of at least the guidewire-management device 2400, the guidewire-management device 2400 includes a handle 2440, the guidewire 102 disposed in a sterile barrier (e.g., the bag 104 or the splittable casing 1204), a first sleeve 2410 formed in a distal portion of the handle 2440, a second sleeve 2420 formed in a proximal portion of the handle 2440, and a tether 2460 coupled to a proximal portion of the guidewire 102.

Notwithstanding possible differences in one or more design elements such as a tether channel 2461 extending through at least a portion of the handle 2440 including a tether line 2462 (e.g., a cord, a wire, etc.) of the guidewire-management device 2400, the handle 2440 is similar to the handle 640 set forth above. As such, the description set forth above for the handle 640 should be understood to extend to the handle 2440 as if the handle 2440 was included in the description of the handle 640.

Notwithstanding possible differences in one or more design elements, the first sleeve 2410 is similar to the first sleeve 110, 610, or 710 set forth above. As such, the description set forth above for the first sleeves 110, 610, and 710 should be understood to extend to the first sleeve 2410 as if the first sleeve 2410 was included in the description of the first sleeves 110, 610, and 710.

Notwithstanding possible differences in one or more design elements, the second sleeve 2420 is similar to the second sleeve 120, 620, or 720 set forth above. As such, the description set forth above for the second sleeves 120, 620, and 720 should be understood to extend to the second sleeve 2420 as if the second sleeve 2420 was included in the description of the second sleeves 120, 620, and 720.

The guidewire-management device 2200 or 2300 can include a membrane 2406 or a capsule 2446 extending between the first sleeve 2410 and the second sleeve 2420 over the guidewire 102, thereby maintaining sterility of the guidewire 102 between the first sleeve 2410 and the second sleeve 2420 subsequent to removal of the bag 104 or the splittable casing 1204, which occurs in the proximal portion of the handle 2440 in the bore 2422. If the guidewire-management device 2400 includes the membrane 2406, the guidewire-management device 2400 can further include a thumb wheel or a ridge such as the ridge 2042 or 2142 set forth above with respect to the guidewire-management device 2000 or 2100. While the tether 2460 is configured for distally feeding the guidewire 102 out of the guidewire-management device 2400 as set forth below, the thumb wheel can be configured for at least proximally feeding the guidewire 102 into the guidewire-management device 2400. Likewise, the ridge can be configured for at least proximally feeding the guidewire 102 into the guidewire-management device 2400 as set forth above with respect to at least the guidewire-management device 2000 or 2100. If the guidewire-management device 2400 includes the capsule 2446, the guidewire-management device 2400 can further include a knob coupled to a guidewire-gripping wheel such as the knob 1744 and the guidewire-gripping wheel 1742 set forth above with respect to the guidewire-management device 1700. While the tether 2460 is configured for distally feeding the guidewire out of the guidewire-management device 2400 as set forth below, the knob and guidewire-gripping wheel can be configured for at least proximally feeding the guidewire 102 into the guidewire-management device 2400 as set forth above with respect to at least the guidewire-management device 1700.

When the guidewire 102 is disposed in the bag 104, a proximal portion of the tether line 2462 is coupled to a proximal portion of the guidewire 102. In addition, a distal portion of the tether line 2462 extends from its point of attachment to the guidewire 102, through the tether channel 2461 extending through the handle 2440, and out an opening in the handle 2440. The distal portion of the tether line 2462 such as a distal end thereof can be coupled to a tether handle 2464 as shown. The tether 2460 is configured to distally feed the guidewire 102 out of the guidewire-management device 2400 by way of the first sleeve 2410 when the tether line 2462 is pulled out of the opening in the handle 2440 and away from the guidewire-management device 2400. As an alternative to the tether handle 2460, the distal portion of the tether line 2462 is coupled to a slider disposed in a slot of the handle 2440, thereby providing an alternative user interface for at least distally feeding the guidewire 102 out of the guidewire-management device 2400 as set forth above for the guidewire-management device 2400. In concert with pulling the tether line 2462 out of the opening in the handle 2440 or advancing the slider, the guidewire 102 splits out of the bag 104 in the second sleeve 2420, propagates to the first sleeve 2410, and out of the guidewire-management device 2400 the by way of the first sleeve 2410, whereas the bag 104 pleats in the bore 2422 of the second sleeve 2420 at a time the guidewire 102 splits out of the bag 104. Proximally feeding the guidewire 102 into the guidewire-management device 2400 by way of the first sleeve 2410 can be effectuated by pushing the tether line 2462 of the tether 2460 into the tether channel 2461 if the tether line 2462 is sufficiently stiff (e.g., a wire) or pressing the slider into a narrowed slider channel of the handle 2440 inboard of the slot and simultaneously moving the slider proximally. Alternatively, proximally feeding the guidewire 102 into the guidewire-management device 2400 by way of the first sleeve 2410 can be effectuated by the thumb wheel, the ridge, or the knob and guidewire-gripping wheel depending upon which feature the guidewire-management device 2400 includes, if any. Without a sufficiently stiff tether line 2362 or any one of the slider, thumb wheel, the ridge, or the knob and guidewire-gripping wheel, the guidewire-management device 2400 is configured for removing the guidewire 102 from a patient by hand.

When the guidewire 102 is disposed in the splittable casing 1204, the tether line 2462 is the splittable casing 1204 split off the guidewire 102 akin to that of the guidewire-management device 2200. In addition, a distal portion of the tether line 2462 extends from its point of attachment to the guidewire 102 (e.g., in the bore 2422), through the tether channel 2461 extending through the handle 2440, and out the opening in the handle 2440. The distal portion of the tether line 2462 such as the distal end thereof can be coupled to the tether handle 2464 as shown. The tether 2460 is configured to distally feed the guidewire 102 out of the guidewire-management device 2400 by way of the first sleeve 2410 when the tether line 2462 is pulled out of the opening in the handle 2440 and away from the guidewire-management device 2400. As an alternative to the tether handle 2460, the distal portion of the tether line 2462 is coupled to the slider disposed in the slot of the handle 2440 set forth above. In concert with pulling the tether line 2462 out of the opening in the handle 2440 or advancing the slider, additional splittable casing 1204 splits off the guidewire 102 in the second sleeve 2420 (e.g. in the bore 2422) before the guidewire 102 propagates to the first sleeve 2410, and out of the guidewire-management device 2400 the by way of the first sleeve 2410. Proximally feeding the guidewire 102 into the guidewire-management device 2400 by way of the first sleeve 2410 can be effectuated by the slider, thumb wheel, the ridge, or the knob and guidewire-gripping wheel depending upon which feature the guidewire-management device 2400 includes, if any. Without any one of the thumb wheel, the ridge, or the knob and guidewire-gripping wheel, the guidewire-management device 2400 is configured for removing the guidewire 102 from a patient by hand.

Adverting to FIGS. 18-23 to describe some of the unique features of at least the guidewire-management device 2600, the guidewire-management device 2600 includes a handle 2640, the guidewire 102, a tether line 2662 at least partially disposed in a sterile barrier 104 (e.g., the bag 104) and coupled to a proximal portion of the guidewire 102, a first sleeve 2610 formed in a distal portion of the handle 2640, a second sleeve 2620 formed in a proximal portion of the handle 2640, a third sleeve 2611 in the distal portion of the handle 2640 adjacent the first sleeve 2610, a fourth sleeve 2621 in the proximal portion of the handle 2640 adjacent the second sleeve 2620, a thumb wheel 2642 between the first sleeve 2610 and the second sleeve 2620, and a guidewire-tether conduit 2650 coupled to the proximal portion of the handle 2640.

Notwithstanding possible differences in one or more design elements such as a tether channel 2661 extending through at least a portion of the handle 2640 including a drive wire or tether line 2662 of the guidewire-management device 2600, the handle 2640 is similar to the handle 640 set forth above. In addition, the handle 2640 is similar to the handle 1740 in that the guidewire 102 extends between the first sleeve 2610 and the second sleeve 2620 but is entirely disposed within the handle 2640 adjacent the tether channel 2661, which handle 2640 functions as an extension of the sterile barrier 104 to maintain sterility of the guidewire 102 between the first sleeve 1710 and the second sleeve 1720. As such, the description set forth above for the handles 640 and 1740 should be understood to extend to the handle 2640 as if the handle 2640 was included in the description of the handles 640 and 1740.

A proximal portion of the tether line 2662 is coupled to the proximal portion of the guidewire 102 by a slug 2666 or some other mass (e.g., a ball), to which the tether line 2662 and the guidewire 102 are fixedly attached (e.g., welded). Alternatively, the proximal portion of the tether line 2662 is fixedly attached (e.g., welded) directly to the proximal portion of the guidewire 102. Regardless, the proximal portion of the tether line 2662 extends from the slug 2666 (or the like) or where it is directly coupled to the proximal portion of the guidewire 102, through the sterile barrier 104 in the guidewire-tether conduit 2650, through the tether channel 2661 extending through the handle 2640, and out an opening of the third sleeve 2611 such that the tether line 2662 never comes into contact with the guidewire 102 except for in embodiments where the proximal portion of the tether line 2662 is fixedly attached (e.g., welded) directly to the proximal portion of the guidewire 102.

The tether line 2662 is configured to distally feed the guidewire 102 out of the guidewire-management device 2600 by way of the first sleeve 2610 when the tether line 2662 is pulled out of the opening of the third sleeve 2611 and away from the guidewire-management device 2600. The guidewire-tether conduit 2650 is configured to facilitate distally feeding the guidewire 102 out of the guidewire-management device 2600 by limiting the degrees of freedom the tether line 2662 and the guidewire 102 would otherwise have to such distal feeding (as well as proximal feeding. In concert with pulling the tether line 2662 out of the third sleeve 2611, the sterile barrier 104 in the guidewire-tether conduit 2650 pleats in a distal portion of the guidewire-tether conduit 2650. The tether line 2662 is also configured to proximally feed the guidewire 102 into the guidewire-management device 2600 by way of the first sleeve 2610 when the tether line 2662 is pushed toward the guidewire-management device 2600 and into the opening of the third sleeve 2611. In concert with pushing the tether line 2662 into of the third sleeve 2611, the sterile barrier 104 in the guidewire-tether conduit 2650 unpleats from the distal portion of the guidewire-tether conduit 2650 and recovers the guidewire 102 to maintain sterility of the guidewire 102.

Notwithstanding possible differences in one or more design elements, the first sleeve 2610 is similar to the first sleeve 110, 610, or 710 set forth above. As such, the description set forth above for the first sleeves 110, 610, and 710 should be understood to extend to the first sleeve 2610 as if the first sleeve 2610 was included in the description of the first sleeves 110, 610, and 710.

Notwithstanding possible differences in one or more design elements, the second sleeve 2620 is similar to the second sleeve 120, 620, or 720 set forth above. As such, the description set forth above for the second sleeves 120, 620, and 720 should be understood to extend to the second sleeve 2620 as if the second sleeve 2620 was included in the description of the second sleeves 120, 620, and 720.

The third sleeve 2611 is configured with a lumen for distally pulling, or advancing, the tether line 2662 out of the guidewire-management device 2600. The lumen of the third sleeve 2611 is coincident with a portion of the tether channel 2661. The third sleeve 2611 is also configured for proximally feeding, or withdrawing, the tether line 2662 into the guidewire-management device 2600.

The fourth sleeve 2621 is configured with a lumen for distally pulling, or advancing, the tether line 2662 in concert with the third sleeve 2611 such as distally feeding the tether line 2662 out of the guidewire-management device 2600. The lumen of the fourth sleeve 2621 is coincident with a portion of the tether channel 2661. The third sleeve 2611 is also configured for proximally feeding, or withdrawing, the tether line 2662 in concert with the third sleeve 2611 such as proximally feeding the tether line 2662 out of the guidewire-management device 2600.

Notwithstanding possible differences in one or more design elements, the thumb wheel 2642 is similar to the thumb wheel 642 or 742 set forth above. As such, the description set forth above for the thumb wheels 642 and 742 should be understood to extend to the thumb wheel 2642 as if the thumb wheel 2642 was included in the description of the thumb wheels 642 and 742. However, the thumb wheel 2642 is configured to assist in distally feeding the tether line 2662 (not the guidewire 102) out of the guidewire-management device 2600 by way of the third sleeve 2611 when the thumb wheel 2642 is used instead of pulling the tether line 2662. The thumb wheel 2642 can provide more fine-tuned distal feeding of the tether line 2662 and, hence, the guidewire 102, over pulling the tether line 2662. The thumb wheel 2642 is also configured to assist in proximally feeding the tether line 2662 into the guidewire-management device 2600 by way of the third sleeve 2611.

In concert with the thumb wheel 2642 or by pulling the tether line 2662, the guidewire-tether conduit 2650 is configured to feed both the guidewire 102 and the tether line 2662 into the guidewire-management device 2600 while distally feeding the guidewire 102 out of the guidewire-management device 2600. The guidewire-tether conduit 2650 can be opaque or translucent. When the guidewire-tether conduit 2650 is translucent, the guidewire-tether conduit 2650 is configured for viewing both the guidewire 102 and the tether line 2662 while feeding the guidewire 102 and the tether line 2662 into the guidewire-management device 2600. Likewise, in concert with the thumb wheel 2642, the guidewire-tether conduit 2650 is configured to collect both the guidewire 102 and the tether line 2662 therein while proximally feeding the guidewire 102 into the guidewire-management device 2600. Again, the guidewire-tether conduit 2650 can be opaque or translucent. When the guidewire-tether conduit 2650 is translucent, the guidewire-tether conduit 2650 is configured for viewing both the guidewire 102 and the tether line 2662 while collecting the guidewire 102 and the tether line 2662 in the guidewire-tether conduit 2650.

Adverting to FIG. 24 to describe some of the unique features of at least the guidewire-management device 2700, the guidewire-management device 2700 includes a handle 2740, the guidewire 102, a first sleeve 2710 formed in a distal portion of the handle 2740, a second sleeve 2720 formed in a proximal portion of the handle 2740, and a combination of an exposed thumb wheel 2742 coupled to a concealed guidewire-gripping wheel 2744 between the first sleeve 2710 and the second sleeve 2720, the concealed guidewire-gripping wheel 2744 configured to grip the guidewire 102 and distally feed the guidewire 102 out of the guidewire-management device 2700 or into the guidewire-management device 2700 by way of the first sleeve 2710 when the exposed thumb wheel 2742 is turned. The guidewire 102 extends between the first sleeve 2710 and the second sleeve 2720 but is disposed within the handle 2740, which functions as a sterile barrier to maintain sterility of the guidewire 102 between the first sleeve 2710 and the second sleeve 2720. In addition to the handle 2740, itself, the guidewire-management device 2700 includes a guidewire conduit 2750 coupled to the second sleeve 2720 configured to maintain sterility of the guidewire 102 outside of the handle 2740 including the first and second sleeves 2710 and 2720. Because both the handle 2740 and the guidewire conduit 2750 are configured to maintain sterility of the guidewire 102, a sterile barrier such as the bag 104 or the splittable casing 1204 is not needed for the guidewire-management device 2700.

Notwithstanding possible differences in one or more design elements, the handle 2740 is similar to the handle 640 set forth above, although the handle 2740 includes features akin to the handle 1740 in that handle 2740 is configured to maintain the sterility of the guidewire 102. In addition, as opposed to being ambidextrous, the handle 2740 might be better suited for use with a clinician's right hand in view of the extension of the exposed thumb wheel 2742 from a side of the handle 2740 that would be used by a left-handed clinician. Regardless, the description set forth above for the handle 640 should be understood to extend to the handle 2740 as if the handle 2740 was included in the description of the handle 640. This includes the description for the channel 641 as the handle 2740 analogously includes a channel 2741.

Notwithstanding possible differences in one or more design elements, the first sleeve 2710 is similar to the first sleeve 110, 610, or 710 set forth above. As such, the description set forth above for the first sleeves 110, 610, and 710 should be understood to extend to the first sleeve 2710 as if the first sleeve 2710 was included in the description of the first sleeves 110, 610, and 710.

Notwithstanding possible differences in one or more design elements, the second sleeve 2720 is similar to the second sleeve 120, 620, or 720 set forth above. As such, the description set forth above for the second sleeves 120, 620, and 720 should be understood to extend to the second sleeve 2720 as if the second sleeve 2720 was included in the description of the second sleeves 120, 620, and 720.

A combination of the exposed thumb wheel 2742 and the concealed guidewire-gripping wheel 2744 is configured for distally feeding the guidewire 102 out of the guidewire-management device 2700 or proximally feeding the guidewire 102 into the guidewire-management device 2700. Indeed, the exposed thumb wheel 2742 includes an axle (e.g., as a unitary piece) disposed in the handle 2740 to which axle the concealed guidewire-gripping wheel 2744 is fixedly coupled such that the concealed guidewire-gripping wheel 2744 rotates with the exposed thumb wheel 2742 when the exposed thumb wheel 2742 is rotated relative to the handle 2740. Alternatively, the concealed guidewire-gripping wheel 2744 includes an axle (e.g., as a unitary piece) disposed in the handle 2740 to which axle the exposed thumb wheel 2742 is fixedly coupled such that the concealed guidewire-gripping wheel 2744 rotates with the exposed thumb wheel 2742 when the exposed thumb wheel 2742 is rotated relative to the handle 2740. Further alternatively, the exposed thumb wheel 2742 and the concealed guidewire-gripping wheel 2744 are independently fixedly coupled to an axle disposed in the handle 2740 such that the concealed guidewire-gripping wheel 2744 rotates with the exposed thumb wheel 2742 when the exposed thumb wheel 2742 is rotated relative to the handle 2740. Even further alternatively, the exposed thumb wheel 2742 and the concealed guidewire-gripping wheel 2744 are a unitary piece including an axle disposed in the handle 2740 such that the concealed guidewire-gripping wheel 2744 rotates with the exposed thumb wheel 2742 when the exposed thumb wheel 2742 is rotated relative to the handle 2740. In this way, the combination of the exposed thumb wheel 2742 and the concealed guidewire-gripping wheel 2744 is configured to assist in distally feeding the guidewire 102 out of the guidewire-management device 2700 by way of the first sleeve 2710 such as when the exposed thumb wheel 2742 is rotated toward the first sleeve 2710. The combination of the exposed thumb wheel 2742 and the concealed guidewire-gripping wheel 2744 is configured to assist in proximally feeding the guidewire 102 into the guidewire-management device 2700 by way of the first sleeve 2710 such as when the exposed thumb wheel 2742 is rotated toward the second sleeve 2720. The concealed guidewire-gripping wheel 2744 includes teeth configured to gently press the guidewire 102 against a compression wheel 2746 and grip the guidewire 102 using the resulting friction for distally feeding the guidewire 102 out of the guidewire-management device 2700 or proximally feeding the guidewire 102 into the guidewire-management device 2700.

The guidewire conduit 2750 is configured to distally feed the guidewire 102 into the guidewire-management device 2700 by way of the second sleeve 2720 while distally feeding the guidewire 102 out of the guidewire-management device 2700, as well as collect the guidewire 102 back in the guidewire conduit 2750 by way of the second sleeve 2720 while proximally feeding the guidewire 102 into the guidewire-management device 2700. The guidewire conduit 2750 can be opaque or translucent depending upon a chosen polymeric material. When the guidewire conduit 2750 is translucent, the guidewire conduit 2750 is configured for viewing the guidewire 102 while distally feeding the guidewire 102 into the guidewire-management device 2700 or collecting the guidewire 102 back in the guidewire conduit 2750 while proximally feeding the guidewire 102 into the guidewire-management device 2700.

While not shown, the guidewire-management device 2700 can further include one or more guidewire-conduit clips configured to hold different portions of the guidewire conduit 2750 therein. Advantageously, the guidewire-conduit clips can hold the guidewire conduit 2750 in a coiled configuration, thereby packing the otherwise elongate guidewire conduit 2750 into a compact space.

METHODS

A method of the guidewire-management device 100, 300, or 600 includes a connecting step of connecting the first sleeve 110 or 610 of the guidewire-management device 100, 300, or 600 to a hub of a medical device (e.g., a hollow needle) inserted into an insertion site of a patient.

The method further includes an advancing step of advancing the guidewire 102 of the guidewire-management device 100, 300, or 600 from the first sleeve 110 or 610 through the hub of the medical device and into the insertion site of the patient. The seal (e.g., the 'O'-ring 114 or 714) in the first sleeve 110 or 610 blocks fluid (e.g., air) from escaping the guidewire-management device 100, 300, or 600 when advancing the guidewire 102 through the hub of the medical device and into the insertion site of the patient.

The advancing step can include pinching the guidewire 102 within the sterile barrier 104 or 304 and advancing the guidewire 102 into the first sleeve 110 by hand. The advancing can alternatively include pressing the guidewire 102 within the sterile barrier 104 onto the thumb wheel 742 and rolling the thumb wheel 742 to advance the guidewire 102 into the first sleeve 610.

Indeed, the guidewire 102 can be advanced into the first sleeve 110 or 610 and out of the guidewire-management device 100 or 600 by pinching a combination of the guidewire 102 within the bag 104 or pressing the guidewire 102 within the bag 104 against the thumb wheel 742, advancing the guidewire 102 into the first sleeve 110 by hand or by rolling the thumb wheel 742, releasing the combination of the guidewire 102 within the bag 104, and repeating the foregoing as necessary. The guidewire 102 can be advanced into the first sleeve 110 and out of the guidewire-management device 300 by pinching a combination of the guidewire 102 within the boot 304, advancing the guidewire 102 into the first sleeve 110 by hand, releasing the combination of the guidewire 102 within the boot 304, and repeating the foregoing as necessary.

The method can further include a ceasing step of ceasing to advance the guidewire 102 into the insertion site of the patient when the ball end of the guidewire 102 is captured in the constriction 124 of the bore 122 in the second sleeve 120 of the guidewire-management device 100 or 300. Likewise, the ceasing step can include ceasing to advance the guidewire 102 into the insertion site of the patient when the ball end of the guidewire 102 is captured in the recess 724 in the second sleeve 620 of the guidewire-management device 600.

The method further includes withdrawing the guidewire 102 from the insertion site of the patient through the hub of the medical device and into the first sleeve 110 or 610. The seal (e.g., the 'O'-ring 114 or 714) in the first sleeve 110 or 610 blocks fluid (e.g., blood) from entering the guidewire-management device 100, 300, or 600 when withdrawing the guidewire 102 from the insertion site.

Indeed, the guidewire 102 can be withdrawn into the guidewire-management device 100 or 600 through the first sleeve 110 or 610 by pinching the combination of the guidewire 102 within the bag 104 or pressing the guidewire 102 within the bag 104 against the thumb wheel 742, withdrawing the guidewire 102 from the first sleeve 110 by hand or by rolling the thumb wheel 742, releasing the combination of the guidewire 102 within the bag 104, and repeating the foregoing as necessary. The guidewire 102 can be withdrawn into the guidewire-management device 300 through the first sleeve 110 by pinching the combination of the guidewire 102 within the boot 304, withdrawing the guidewire 102 from the first sleeve 110 by hand, releasing the combination of the guidewire 102 within the boot 304, and repeating the foregoing as necessary.

The method can further include ceasing to withdraw the guidewire 102 from the insertion site of the patient when the proximal end or the ball end of the guidewire 102 abuts the plug 152 in the proximal portion of the guidewire conduit 150 of the guidewire-management device 100 or 300.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A guidewire-management device, comprising:
   a handle;
   a guidewire;
   a first sleeve formed in a distal portion of the handle;
   a second sleeve formed in a proximal portion of the handle, wherein at least a length of the guidewire extending between the first sleeve and the second sleeve is disposed within a sterile barrier configured to maintain sterility of the guidewire;
   a gapped guidewire conduit coupled to the second sleeve, a gap in the gapped guidewire conduit configured to allow the guidewire to be grasped and distally fed into the guidewire-management device by way of the second sleeve, wherein the gapped guidewire conduit includes a plug configured to allow a distal end of the guidewire to enter the first sleeve and prevent proximal displacement of the guidewire out of the first sleeve; and
   a number of clips disposed along the gapped guidewire conduit, the number of clips configured to secure portions of the gapped guidewire conduit together in a coiled configuration, wherein a first clip is positioned on a first side of the gap and a second clip is positioned on a second side of the gap opposite the first side.

2. The guidewire-management device of claim 1, wherein the first sleeve has a distal portion configured as a male connector with a Luer taper for connecting the first sleeve to a complementary female connector.

3. The guidewire-management device of claim 1, wherein the first sleeve is configured to straighten a 'J'-shaped tip in a distal portion of the guidewire as the 'J'-shaped tip of the guidewire enters the first sleeve when proximally feeding the guidewire into the guidewire-management device.

4. The guidewire-management device of claim 1, wherein the second sleeve has a proximal portion including a bore with a constriction configured to capture a ball end of the guidewire and stop the guidewire from completely passing through the second sleeve.

5. The guidewire-management device of claim 1, wherein the sterile barrier is a pleated bag over an entirety of the guidewire excepting that within or distal to the first sleeve configured to pleat as the pleated bag is inserted into a bore in a proximal portion of the first sleeve while distally feeding the guidewire out of the guidewire-management device.

6. The guidewire-management device of claim 1, wherein the sterile barrier is a splittable casing over an entirety of the guidewire excepting that within or distal to the first sleeve, the splittable casing configured to split off the guidewire while distally feeding the guidewire out of the guidewire-management device.

7. The guidewire-management device of claim 6, further comprising a first split sleeve in the distal portion of the handle, the first split sleeve configured to discharge the splittable casing while distally feeding the guidewire out of the guidewire-management device.

8. The guidewire-management device of claim 1, wherein at least the length of the guidewire is sized such that the distal end of the guidewire is disposed within the first sleeve when a proximal end of the guidewire is disposed adjacent the plug.

9. The guidewire-management device of claim 4, wherein a diameter of the ball end is greater than an inside diameter of the sterile barrier.

10. The guidewire-management device of claim 4, wherein a proximal end of the sterile barrier is disposed adjacent the ball end.

* * * * *